(12) United States Patent
Cho et al.

(10) Patent No.: US 11,525,122 B2
(45) Date of Patent: Dec. 13, 2022

(54) MICROORGANISMS WITH ENHANCED CARBON MONOXIDE AVAILABILITY AND USE THEREOF

(71) Applicant: KOREA ADVANCED INSTITUTE OF SCIENCE AND TECHNOLOGY, Daejeon (KR)

(72) Inventors: Byung-Kwan Cho, Daejeon (KR); Yoseb Song, Daejeon (KR); Jongoh Shin, Daejeon (KR); Sangrak Jin, Daejeon (KR); Seulgi Kang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 40 days.

(21) Appl. No.: 17/068,262

(22) Filed: Oct. 12, 2020

(65) Prior Publication Data

US 2021/0123029 A1    Apr. 29, 2021

(30) Foreign Application Priority Data

Oct. 23, 2019 (KR) ........................ 10-2019-0132451

(51) Int. Cl.
*C12P 7/26* (2006.01)
*C12N 9/02* (2006.01)
*C12N 1/20* (2006.01)
*C12R 1/01* (2006.01)

(52) U.S. Cl.
CPC ............. *C12N 9/0008* (2013.01); *C12N 1/20* (2013.01); *C12N 1/205* (2021.05); *C12P 7/26* (2013.01); *C12Y 102/07004* (2013.01); *C12N 2500/02* (2013.01); *C12R 2001/01* (2021.05)

(58) Field of Classification Search
None
See application file for complete search history.

(56) References Cited

U.S. PATENT DOCUMENTS

2020/0239831 A1\* 7/2020 Kim ........................ C12N 1/20
2021/0123029 A1\* 4/2021 Cho ....................... C12N 1/205

OTHER PUBLICATIONS

Drake et al. "Old acetogens, new light." *Annals of the New York Academy of Sciences* 1125.1 (2008): 100.

\* cited by examiner

*Primary Examiner* — Hope A Robinson
(74) *Attorney, Agent, or Firm* — ParkerHighlander, PLLC

(57) ABSTRACT

The present invention relates to a protein variant, a microorganism with enhanced carbon monoxide (CO) availability comprising the variant, and a use thereof.

3 Claims, 6 Drawing Sheets

Specification includes a Sequence Listing.

SEQUENCE LISTING

<160> NUMBER OF SEQ ID NOS: 24

<210> SEQ ID NO 1
<211> LENGTH: 631
<212> TYPE: PRT
<213> ORGANISM: Eubacterium limosum

<400> SEQUENCE: 1

```
Met Ser Asn Glu Leu Leu Glu Phe Asp Val Ile Ala Glu Ala Leu Ile
1               5                   10                  15

Glu Lys Ala Gln Lys Asp Gly Ala Glu Thr Met Trp Asp Arg Lys Ala
            20                  25                  30

Ala Leu Lys Thr Gln Cys Gly Phe Gly Glu Gly Ile Cys Cys Arg
        35                  40                  45

Ile Cys Val Met Gly Pro Cys Arg Val Ser Pro Ser Pro Asp Lys Gly
    50                  55                  60

Ala Gln Arg Gly Ile Cys Gly Ala Asp Arg Asp Thr Ile Val Ala Arg
65                  70                  75                  80

Asn Phe Ala Arg Met Cys Cys Gly Gly Thr Ser Ala His Ser Asp His
                85                  90                  95

Ala Arg Asp Ile Val His Ala Met Tyr His Ser Ser Glu Asp Gly Pro
            100                 105                 110

Phe Lys Ile Arg Glu Glu Gly Lys Leu Arg Lys Ile Ala Ala Glu Trp
        115                 120                 125

Gly Ile Glu Glu Ala Asp Thr Lys Glu Thr Tyr Ala Leu Ala His Glu
    130                 135                 140

Leu Ala Glu Met Ala Leu Met Glu Phe Gly Lys Pro Phe Gly Thr Gln
145                 150                 155                 160

Asn Phe Leu Lys Arg Ala Pro Lys Ser Arg Gln Glu Ile Trp Glu Arg
                165                 170                 175

Glu Asn Ile Ala Pro Arg Ala Ile Asp Gln Glu Val Val Thr Leu Met
            180                 185                 190

His Ser Thr His Met Gly Cys Ala Ser Asp Pro Glu Ser Ile Leu Arg
        195                 200                 205

Arg Ser Leu Arg Thr Ser Met Ser Asp Gly Trp Gly Gly Ser Met Ile
    210                 215                 220

Gly Thr Glu Phe Ser Asp Ile Met Tyr Gly Val Pro Lys Glu Arg Ala
225                 230                 235                 240

Ser Glu Ser Asn Leu Gly Val Ile Asp Pro Glu Gln Val Asn Ile Met
                245                 250                 255

Leu His Gly His Asp Pro Asn Leu Ala Glu Met Ile Ala Val Ala Ser
            260                 265                 270

Lys Asn Pro Glu Leu Ile Glu Met Ala Lys Glu Gln Gly Ala Lys Gly
        275                 280                 285

Ile Asn Val Val Gly Met Cys Cys Thr Gly Asn Glu Met Thr Met Arg
    290                 295                 300

His Gly Ile Lys Ile Ala Gly Asn Phe Tyr Gln Gln Glu Met Ala Ile
305                 310                 315                 320

Ile Thr Gly Ala Val Glu Val Ala Val Val Asp Val Gln Cys Ile Phe
                325                 330                 335
```

```
Pro Ala Leu Pro Lys Leu Ala Lys Ser Tyr His Thr Arg Phe Ile Ser
            340                 345                 350

Thr Ser Pro Lys Ala Lys Ile Ala Gly Asp Met Tyr Ile Glu Phe Asn
        355                 360                 365

Glu Glu Asp Pro Leu Ser Cys Ala Glu Val Ile Lys Thr Ala Val
            370                 375                 380

Met Asn Phe Lys Asn Arg Asp Ala Ser Lys Val Asp Val Pro Glu Leu
385                 390                 395                 400

Lys Ala Glu Thr Ile Val Gly Tyr Ser Val Glu Thr Ile Gly Ala
                405                 410                 415

Leu Asp Arg Val Val Asn Ser Gln Thr Asp Val Thr Gly Thr Val Lys
            420                 425                 430

Pro Leu Gly Asp Leu Val Trp Ala Gly Val Leu Arg Gly Ala Ala Gly
            435                 440                 445

Ile Val Gly Cys Asn Asn Pro Lys Val Glu His Asp Tyr Ala His Ile
            450                 455                 460

Thr Leu Met Lys Glu Leu Ile Lys Asn Asp Val Ile Cys Val Val Thr
465                 470                 475                 480

Gly Cys Ala Ala Gln Ala Ala Lys Ala Gly Leu Leu Lys Leu Glu
                485                 490                 495

Ala Lys Glu Leu Cys Gly Arg Gly Leu Lys Glu Ala Cys Glu Arg Ala
            500                 505                 510

Asn Ile Pro Pro Val Leu His Met Gly Ser Cys Val Asp Ile Ser Arg
            515                 520                 525

Ile Leu His Leu Val Thr Leu Val Ala Asn Glu Arg Gly Val Asp Ile
            530                 535                 540

Ala Glu Leu Pro Val Val Gly Ala Ala Pro Glu Tyr Met Ser Glu Lys
545                 550                 555                 560

Ala Val Ala Ile Ala Ser Tyr Val Val Ser Ser Gly Leu Asn Thr Tyr
                565                 570                 575

Leu Gly Val Met Pro Tyr Val Ser Gly Ser Glu Asn Phe Met Lys Leu
            580                 585                 590

Met Thr Glu Gly Val Lys Glu Trp Thr Gly Ala Ala Tyr Val Phe Glu
            595                 600                 605

Ser Asp Pro Ile Lys Ala Ala Glu Leu Ile Met Ala Asp Ile Glu Asp
            610                 615                 620

Lys Arg Thr Lys Leu Gly Ile
625                 630

<210> SEQ ID NO 2
<211> LENGTH: 1896
<212> TYPE: DNA
<213> ORGANISM: Eubacterium limosum

<400> SEQUENCE: 2
atgagcaatg aattgttaga atttgatgtt atagctgaag ctttaatcga aaaagctcaa      60
aaagatggcg ctgaaaccat gtgggacaga aaagctgctt taaaaaccca gtgtggtttt     120
ggtgaaggcg gtatttgctg tcgtatctgt gttatgggac cttgccgtgt aagcccatcg     180
ccagataaag gcgctcagag aggtatctgt ggtgctgaca gagacaccat cgttgccaga     240
aactttgcaa gaatgtgctg tggtggtaca tccgctcact ctgaccatgc gcgcgatatc     300
gtacatgcaa tgtatcattc ttctgaagat ggtcctttca aaatcagaga agaaggcaaa     360
ttaagaaaaa tcgctgcaga atggggaatt gaagaagcag ataccaaaga aacctacgct     420
```

```
ctggcccatg aacttgcaga atggctttta atggaattcg gtaaaccttt tggaacacag    480
aatttcttaa agagagcgcc taaatcccgt caggaaatct gggaaagaga aaacatcgca    540
cctagagcga ttgaccagga agttgttacc ttaatgcact ccacacatat gggttgtgca    600
agtgatcctg aatccatctt aagacgttct ttaagaacaa gtatgtctga tggctggggc    660
ggttccatga tcggtacaga attctctgac atcatgtacg gtgtaccaaa ggaaagagct    720
tctgaatcaa acttaggtgt tattgatcct gaacaggtaa atatcatgct ccacggacat    780
gatccgaact tggctgaaat gatcgcagtt gcatccaaaa atcctgagct gattgaaatg    840
gcaaaagaac agggcgctaa gggtatcaac gttgtcggta tgtgctgtac tggtaatgaa    900
atgaccatgc gtcacggtat taagatcgcc ggtaacttct accagcagga aatggccatt    960
atcaccggtg ccgttgaagt tgctgttgta gacgttcagt gtatcttccc tgcactgcct   1020
aaattagcta agagctacca tacacgcttt atcagtacat ctccaaaagc aaaaatcgcg   1080
ggggatatgt acattgaatt taatgaagaa gatccattga gctgcgctga agaagtaatc   1140
aaaacagctg ttatgaactt caagaacaga gacgcttcca aggttgatgt accggaactg   1200
aaagctgaaa caattgttgg ttattctgta gaaacaacaa tcggcgcttt agaccgcgtt   1260
gttaactctc agaccgacgt aacaggtacg gttaaacctt taggcgactt agtttgggct   1320
ggtgttttaa gaggcgctgc cggtattgtt ggttgtaaca atcctaaggt cgaacatgac   1380
tatgcccaca tcacattgat gaaagaatta attaaaaacg acgttatctg cgttgttact   1440
ggttgtgcag ctcaggctgc tgctaaagct ggtcttttaa aactggaagc aaaagaactt   1500
tgcggccgtg gtttaaaaga agcctgcgaa agagcgaata ttcctccagt attacatatg   1560
ggttcctgtg ttgatatcag ccgtatcctc cacctggtta ctttagtagc taacgaaaga   1620
ggcgttgata ttgcagaact tccagttgta ggtgccgcac cagaatacat gtctgaaaag   1680
gctgttgcta tcgcatctta cgtagtatca agtggtttaa atacttatct tggtgttatg   1740
ccttatgttt ccggaagtga aaacttcatg aagctgatga ccgaaggtgt taaagaatgg   1800
actggcgctg cttatgtctt tgaatcagat ccaatcaagg ctgctgaatt aatcatggca   1860
gatattgaag acaagagaac aaaactggga atttaa                             1896
```

<210> SEQ ID NO 3
<211> LENGTH: 631
<212> TYPE: PRT
<213> ORGANISM: Eubacterium limosum

<400> SEQUENCE: 3

| Met | Ser | Asn | Glu | Leu | Leu | Glu | Phe | Asp | Val | Ile | Ala | Glu | Ala | Leu | Ile |
|---|---|---|---|---|---|---|---|---|---|---|---|---|---|---|---|
| 1 | | | | 5 | | | | | 10 | | | | | 15 | |

| Glu | Lys | Ala | Gln | Lys | Asp | Gly | Ala | Glu | Thr | Met | Trp | Asp | Arg | Lys | Ala |
|---|---|---|---|---|---|---|---|---|---|---|---|---|---|---|---|
| | | | 20 | | | | | 25 | | | | | 30 | | |

| Ala | Leu | Lys | Thr | Gln | Cys | Gly | Phe | Gly | Glu | Gly | Gly | Ile | Cys | Cys | Arg |
|---|---|---|---|---|---|---|---|---|---|---|---|---|---|---|---|
| | | 35 | | | | | 40 | | | | | 45 | | | |

| Ile | Cys | Val | Met | Gly | Pro | Cys | Arg | Val | Ser | Pro | Ser | Pro | Asp | Lys | Gly |
|---|---|---|---|---|---|---|---|---|---|---|---|---|---|---|---|
| | 50 | | | | | 55 | | | | | 60 | | | | |

| Ala | Gln | Arg | Gly | Ile | Cys | Gly | Ala | Asp | Arg | Asp | Thr | Ile | Val | Ala | Arg |
|---|---|---|---|---|---|---|---|---|---|---|---|---|---|---|---|
| 65 | | | | | 70 | | | | | 75 | | | | | 80 |

| Asn | Phe | Ala | Arg | Met | Cys | Cys | Gly | Gly | Thr | Ser | Ala | His | Ser | Asp | His |
|---|---|---|---|---|---|---|---|---|---|---|---|---|---|---|---|
| | | | | 85 | | | | | 90 | | | | | 95 | |

| Glu | Arg | Asp | Ile | Val | His | Ala | Met | Tyr | His | Ser | Ser | Glu | Asp | Gly | Pro |
|---|---|---|---|---|---|---|---|---|---|---|---|---|---|---|---|
| | | | 100 | | | | | 105 | | | | | 110 | | |

-continued

```
Phe Lys Ile Arg Glu Glu Gly Lys Leu Arg Lys Ile Ala Ala Glu Trp
        115                 120                 125
Gly Ile Glu Glu Ala Asp Thr Lys Glu Thr Tyr Ala Leu Ala His Glu
    130                 135                 140
Leu Ala Glu Met Ala Leu Met Glu Phe Gly Lys Pro Phe Gly Thr Gln
145                 150                 155                 160
Asn Phe Leu Lys Arg Ala Pro Lys Ser Arg Gln Glu Ile Trp Glu Arg
                165                 170                 175
Glu Asn Ile Ala Pro Arg Ala Ile Asp Gln Glu Val Val Thr Leu Met
            180                 185                 190
His Ser Thr His Met Gly Cys Ala Ser Asp Pro Glu Ser Ile Leu Arg
        195                 200                 205
Arg Ser Leu Arg Thr Ser Met Ser Asp Gly Trp Gly Gly Ser Met Ile
    210                 215                 220
Gly Thr Glu Phe Ser Asp Ile Met Tyr Gly Val Pro Lys Glu Arg Ala
225                 230                 235                 240
Ser Glu Ser Asn Leu Gly Val Ile Asp Pro Glu Gln Val Asn Ile Met
                245                 250                 255
Leu His Gly His Asp Pro Asn Leu Ala Glu Met Ile Ala Val Ala Ser
            260                 265                 270
Lys Asn Pro Glu Leu Ile Glu Met Ala Lys Glu Gln Gly Ala Lys Gly
        275                 280                 285
Ile Asn Val Val Gly Met Cys Cys Thr Gly Asn Glu Met Thr Met Arg
    290                 295                 300
His Gly Ile Lys Ile Ala Gly Asn Phe Tyr Gln Glu Met Ala Ile
305                 310                 315                 320
Ile Thr Gly Ala Val Glu Val Ala Val Val Asp Val Gln Cys Ile Phe
                325                 330                 335
Pro Ala Leu Pro Lys Leu Ala Lys Ser Tyr His Thr Arg Phe Ile Ser
            340                 345                 350
Thr Ser Pro Lys Ala Lys Ile Ala Gly Asp Met Tyr Ile Glu Phe Asn
        355                 360                 365
Glu Glu Asp Pro Leu Ser Cys Ala Glu Glu Val Ile Lys Thr Ala Val
    370                 375                 380
Met Asn Phe Lys Asn Arg Asp Ala Ser Lys Val Asp Val Pro Glu Leu
385                 390                 395                 400
Lys Ala Glu Thr Ile Val Gly Tyr Ser Val Glu Thr Thr Ile Gly Ala
                405                 410                 415
Leu Asp Arg Val Val Asn Ser Gln Thr Asp Val Thr Gly Thr Val Lys
            420                 425                 430
Pro Leu Gly Asp Leu Val Trp Ala Gly Val Leu Arg Gly Ala Ala Gly
        435                 440                 445
Ile Val Gly Cys Asn Asn Pro Lys Val Glu His Asp Tyr Ala His Ile
    450                 455                 460
Thr Leu Met Lys Glu Leu Ile Lys Asn Asp Val Ile Cys Val Val Thr
465                 470                 475                 480
Gly Cys Ala Ala Gln Ala Ala Ala Lys Ala Gly Leu Leu Lys Leu Glu
                485                 490                 495
Ala Lys Glu Leu Cys Gly Arg Gly Leu Lys Glu Ala Cys Glu Arg Ala
            500                 505                 510
Asn Ile Pro Pro Val Leu His Met Gly Ser Cys Val Asp Ile Ser Arg
        515                 520                 525
```

```
Ile Leu His Leu Val Thr Leu Val Ala Asn Glu Arg Gly Val Asp Ile
            530                 535                 540

Ala Glu Leu Pro Val Val Gly Ala Ala Pro Glu Tyr Met Ser Glu Lys
545                 550                 555                 560

Ala Val Ala Ile Ala Ser Tyr Val Val Ser Ser Gly Leu Asn Thr Tyr
                565                 570                 575

Leu Gly Val Met Pro Tyr Val Ser Gly Ser Glu Asn Phe Met Lys Leu
                580                 585                 590

Met Thr Glu Gly Val Lys Glu Trp Thr Gly Ala Ala Tyr Val Phe Glu
            595                 600                 605

Ser Asp Pro Ile Lys Ala Ala Glu Leu Ile Met Ala Asp Ile Glu Asp
            610                 615                 620

Lys Arg Thr Lys Leu Gly Ile
625                 630

<210> SEQ ID NO 4
<211> LENGTH: 1896
<212> TYPE: DNA
<213> ORGANISM: Eubacterium limosum

<400> SEQUENCE: 4
atgagcaatg aattgttaga atttgatgtt atagctgaag ctttaatcga aaaagctcaa        60
aaagatggcg ctgaaaccat gtgggacaga aaagctgctt taaaaaccca gtgtggtttt       120
ggtgaaggcg gtatttgctg tcgtatctgt gttatgggac cttgccgtgt aagcccatcg       180
ccagataaag gcgctcagag aggtatctgt ggtgctgaca gagacaccat cgttgccaga       240
aactttgcaa gaatgtgctg tggtggtaca tccgctcact ctgaccatga gcgcgatatc       300
gtacatgcaa tgtatcattc ttctgaagat ggtcctttca aaatcagaga agaaggcaaa       360
ttaagaaaaa tcgctgcaga atggggaatt gaagaagcag ataccaaaga aacctacgct       420
ctggcccatg aacttgcaga aatggcttta atggaattcg gtaaaccttt tggaacacag       480
aatttcttaa agagagcgcc taaatcccgt caggaaatct gggaaagaga aaacatcgca       540
cctagagcga ttgaccagga agttgttacc ttaatgcact ccacacatat gggttgtgca       600
agtgatcctg aatccatctt aagacgttct ttaagaacaa gtatgtctga tggctggggc       660
ggttccatga tcggtacaga attctctgac atcatgtacg gtgtaccaaa ggaaagagct       720
tctgaatcaa acttaggtgt tattgatcct gaacaggtaa atatcatgct ccacggacat       780
gatccgaact ggctgaaaat gatcgcagtt gcatccaaaa atcctgagct gattgaaatg       840
gcaaaagaac agggcgctaa gggtatcaac gttgtcggta tgtgctgtac tggtaatgaa       900
atgaccatgc gtcacggtat taagatcgcc ggtaacttct accagcagga aatggccatt       960
atcaccggtg ccgttgaagt tgctgttgta gacgttcagt gtatcttccc tgcactgcct      1020
aaattagcta agagctacca tacacgcttt atcagtacat ctccaaaagc aaaaatcgcg      1080
ggggatatgt acattgaatt taatgaagaa gatccattga gctgcgctga gaagtaatc       1140 aaaacagctg ttatgaactt caagaacaga gacgcttcca aggttgatgt accggaactg      1200
aaagctgaaa caattgttgg ttattctgta gaaacaacaa tcggcgcttt agaccgcgtt      1260
gttaactctc agaccgacgt aacaggtacg gttaaacctt aggcgacttt agtttgggct      1320
ggtgttttaa gaggcgctgc cggtattgtt ggttgtaaca atcctaaggt cgaacatgac      1380
tatgcccaca tcacattgat gaaagaatta ttaaaaacg acgttatctg cgttgttact      1440
ggttgtgcag ctcaggctgc tgctaaagct ggtctttaa aactggaagc aaaagaactt      1500
```

```
tgcggccgtg gtttaaaaga agcctgcgaa agagcgaata ttcctccagt attacatatg   1560
ggttcctgtg ttgatatcag ccgtatcctc cacctggtta ctttagtagc taacgaaaga   1620
ggcgttgata ttgcagaact tccagttgta ggtgccgcac cagaatacat gtctgaaaag   1680
gctgttgcta tcgcatctta cgtagtatca agtggtttaa atacttatct tggtgttatg   1740
ccttatgttt ccggaagtga aaacttcatg aagctgatga ccgaaggtgt taaagaatgg   1800
actggcgctg cttatgtctt tgaatcagat ccaatcaagg ctgctgaatt aatcatggca   1860
gatattgaag acaagagaac aaaactggga atttaa                             1896
```

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5

```
caaaagccct taaataggcg                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6

```
aatgtcaagc tgtatttgcg                                                 20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7

```
gtgtctggca aatggtattg                                                 20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8

```
tttaatcacg gtatcacccc                                                 20
```

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9

```
gtgtgaacat tgcacagtc                                                  19
```

<210> SEQ ID NO 10
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 10
caatctctgg aaaaagctgc                                              20

<210> SEQ ID NO 11
<211> LENGTH: 18
<212> TYPE: DNA
<213> ORGANISM: Artificial Sequence
<220> FEATURE:
<223> OTHER INFORMATION: Synthetic primer

<400> SEQUENCE: 11
actggcactt gacaccgc                                                18

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
ataacagcaa cacctggg                                                18

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
atgcagactc cgttctgg                                                18

<210> SEQ ID NO 14
<211> LENGTH: 18
<212> TYPE: DNA
<213> ORGANISM: Artificial Sequence
<220> FEATURE:
<223> OTHER INFORMATION: Synthetic primer

<400> SEQUENCE: 14
gttaaagaat ggactggc                                                18

<210> SEQ ID NO 15
<211> LENGTH: 54
<212> TYPE: DNA
<213> ORGANISM: Artificial Sequence
<220> FEATURE:
<223> OTHER INFORMATION: Synthetic primer

<400> SEQUENCE: 15
ccatacgcgt ggatccctcg agatgttgac aaaagcaaca aagaacaaa aatc         54

<210> SEQ ID NO 16
<211> LENGTH: 48
<212> TYPE: DNA
<213> ORGANISM: Artificial Sequence
<220> FEATURE:
<223> OTHER INFORMATION: Synthetic primer

<400> SEQUENCE: 16
atgattacga attcgagctc ctagagagct tcgttttca tgagttcc                48
```

<210> SEQ ID NO 17
<211> LENGTH: 48
<212> TYPE: DNA
<213> ORGANISM: Artificial Sequence
<220> FEATURE:
<223> OTHER INFORMATION: Synthetic primer

<400> SEQUENCE: 17
cggtacccgg ggatccacgc gtatggaaac taatagctcg tgcgattg            48

<210> SEQ ID NO 18
<211> LENGTH: 39
<212> TYPE: DNA
<213> ORGANISM: Artificial Sequence
<220> FEATURE:
<223> OTHER INFORMATION: Synthetic primer

<400> SEQUENCE: 18
atgcctgcag gtcgacctaa ccctcagccg cacggatag                      39

<210> SEQ ID NO 19
<211> LENGTH: 33
<212> TYPE: DNA
<213> ORGANISM: Artificial Sequence
<220> FEATURE:
<223> OTHER INFORMATION: Synthetic primer

<400> SEQUENCE: 19
acatctcgag ggatcccatt taccgggcca agc                            33

<210> SEQ ID NO 20
<211> LENGTH: 43
<212> TYPE: DNA
<213> ORGANISM: Artificial Sequence
<220> FEATURE:
<223> OTHER INFORMATION: Synthetic primer

<400> SEQUENCE: 20
tagtttccat acgcgtttcc tccttgaaac aagacgttct gag                 43

<210> SEQ ID NO 21
<211> LENGTH: 41
<212> TYPE: DNA
<213> ORGANISM: Artificial Sequence
<220> FEATURE:
<223> OTHER INFORMATION: Synthetic primer

<400> SEQUENCE: 21
ccggtaaatg ggatcccttta agcgtgaagt gaaaagaatg g                  41

<210> SEQ ID NO 22
<211> LENGTH: 43
<212> TYPE: DNA
<213> ORGANISM: Artificial Sequence
<220> FEATURE:
<223> OTHER INFORMATION: Synthetic primer

<400> SEQUENCE: 22
ttgtcaacat ctcgagttcc tccttgaaac aagacgttct gag                 43

<210> SEQ ID NO 23
<211> LENGTH: 22
<212> TYPE: DNA
<213> ORGANISM: Artificial Sequence
<220> FEATURE:
<223> OTHER INFORMATION: Synthetic primer

```
<400> SEQUENCE: 23
cagttaaacg gccgactgct tg                                              22

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
gtccagccgg ttaaacgtgc                                                 20
```

MICROORGANISMS WITH ENHANCED CARBON MONOXIDE AVAILABILITY AND USE THEREOF

This application claims priority to Korean Application No. 10-2019-0132451, filed Oct. 23, 2019. The entire text of the above referenced disclosure is specifically incorporated herein by reference.

TECHNICAL FIELD

The present invention relates to a protein variant, a microorganism with enhanced carbon monoxide (CO) availability comprising the variant, and a use thereof.

BACKGROUND ART

The recently emerging carbon resource technology is a technology that utilizes carbon monoxide, carbon dioxide, methane, natural gas, etc. generated from fossil fuels, etc. as a raw material. The technology has been highlighted as a new industry creation item because it has effects such as greenhouse gas reduction, energy self-sufficiency, etc.

Waste gas (synthetic gas) is a mixed gas consisting of carbon monoxide (CO), carbon dioxide ($CO_2$), and hydrogen ($H_2$) obtained through a gasification process of various carbon-based raw materials (e.g., waste, coal, coke, lower hydrocarbon gas, naphtha, heavy oil, etc.) and it is called syngas or waste gas. A group of microorganisms that produce acetic acid through anaerobic metabolism using syngas or sugar as carbon and energy sources is called "acetogen". Acetogen has the possibility of producing organic acids (e.g., butyric acid) and bioalcohols (e.g., ethanol and butanol) in addition to acetic acid (i.e., a main product), by using waste gas as carbon and energy sources (H L Drake et al., *Annals of the New York Academy of Sciences*, 1125: 100, 2008).

Thus far, more than 100 acetogens are known in the art, but only a few strains are known to consume waste gas to produce 4-carbon organics (e.g., butyric acid). In addition, the establishment of a genetic engineering system suitable for acetogen (i.e., a gram-positive anaerobic strain) is very complex and self-growth of an acetogen at a high CO concentration is extremely limited. Therefore, metabolic engineering for increasing the productivity of metabolites with respect to an acetogen and its subsequent development into commercialization have rarely been successful.

Under these circumstances, the present inventors, in an effort to develop a microorganism whose growth level is not deteriorated even under the condition of a high CO concentration, have attempted the evolution of a microorganism by applying a CO concentration to the microorganism as a stress. As a result, they have discovered that the microorganism has adapted to the environment of the high CO concentration and thereby includes a mutation in the CODH/ACS protein complex, and they have confirmed that this protein variant is involved in the enhancement of CO availability of the microorganism, thereby completing the present invention.

DISCLOSURE

Technical Problem

An object of the present invention is to provide a protein variant, wherein the $97^{th}$ residue from the N-terminus of SEQ ID NO: 1, alanine (A), is substituted with a different amino acid; and a microorganism comprising the same.

Another object of the present invention is to provide a method for preparing a microorganism with enhanced CO availability.

Still another object of the present invention is to provide a method for preparing a compound, comprising a step of culturing the microorganism.

Technical Solution

The present invention is described in detail as follows. Meanwhile, respective descriptions and embodiments disclosed in the present invention may also be applied to other descriptions and embodiments. That is, all combinations of various elements disclosed in the present invention fall within the scope of the present invention. Further, the scope of the present invention cannot be considered to be limited by the specific description below.

Additionally, those skilled in the art will be able to recognize or confirm, based on routine experimentation, many equivalents to the specific embodiments of the present invention described in this application, and such equivalents are intended to be included in the present invention.

An aspect of the present invention provides a protein variant, wherein the $97^{th}$ residue from the N-terminus of SEQ ID NO: 1, alanine (A), is substituted with a different amino acid.

The protein of SEQ ID NO: 1 above may be a protein, which has an activity of carbon monoxide dehydrogenase (hereinafter, CODH), derived from *Eubacterium limosum*.

Meanwhile, in the present invention, although the protein of SEQ ID NO: 1 is described as a representative example of a protein having a CODH activity, it does not exclude an addition of a meaningless sequence upstream or downstream of the amino acid sequence of SEQ ID NO: 1, a mutation that may occur naturally, or a silent mutation thereof, and it is apparent to one of ordinary skill in the art that any protein, which has an activity identical or corresponding to the protein including the amino acid sequence of SEQ ID NO: 1, belongs to the protein of the present invention.

In a specific embodiment, the CODH protein of the present invention may be a protein consisting of the amino acid sequence of SEQ ID NO: 1, or a protein consisting of an amino acid sequence having a homology or identity to the amino acid sequence of SEQ ID NO: 1 of 80%, 90%, 95%, 97%, or higher. Additionally, it is apparent that any protein having an amino acid sequence with deletion, modification, substitution, or addition in part of the sequence can also belong to the scope of the proteins of the present invention to be a subject for mutation, as long as the protein has an amino acid sequence with such homologies or identities and exhibits an effect corresponding to the above protein.

That is, in the present invention, even in a case where it is described as "protein or polypeptide having an amino acid sequence of a particular SEQ ID NO" or "protein or polypeptide consisting of an amino acid sequence of a particular SEQ ID NO", it is apparent that any protein having an amino acid sequence with deletion, modification, substitution, or addition in part of the sequence can also be used in the present invention, as long as the protein has an activity identical or corresponding to that of the polypeptide consisting of the amino acid sequence of the corresponding SEQ ID NO. For example, it is apparent that the "polypeptide consisting of the amino acid sequence of SEQ ID NO: 1" can also belong to the "polypeptide comprising the amino acid sequence of SEQ ID NO: 1", as long as the polypeptide has an activity identical or corresponding thereto.

As used herein, the term "variant" refers to a protein, in which at least one amino acid in the conservative substitution and/or modification is different from that of the recited sequence, but the functions or properties of the protein are maintained. A variant differs from the sequence identified by several amino acid substitutions, deletions, or additions. Such a variant can be generally identified by modifying one or more amino acids in the amino acid sequence of the protein above and by evaluating the properties of the modified protein above. That is, the ability of a variant may be increased, unchanged, or reduced compared to that of its native protein. Additionally, some variants may include those in which one or more parts (e.g., an N-terminal leader sequence or a transmembrane domain) are removed. Other variants may include variants in which part of the N-terminus and/or C-terminus of a mature protein is removed. The term "variant" may also be used interchangeably with "modification", "modified protein", "modified polypeptide", "mutant", "mutein", "divergent", "variant", etc., but the term to be used is not limited thereto and any term may be used, as long as it is used in a sense of being mutated.

As used herein, the term "conservative substitution" refers to substitution of one amino acid with a different amino acid that has similar structural and/or chemical properties. The variant may have, for example, one or more conservative substitutions while still retaining one or more biological activities. Such amino acid substitutions may generally occur based on similarity in polarity, charge, solubility, hydrophobicity, hydrophilicity, and/or amphipathic nature of residues. For example, among the electrically charged amino acids, positively-charged (basic) amino acids include arginine, lysine, and histidine; negatively-charged (acidic) amino acids include glutamic acid and aspartic acid. Among the uncharged amino acids, nonpolar amino acids include glycine, alanine, valine, leucine, isoleucine, methionine, phenylalanine, tryptophan, and proline; polar or hydrophilic amino acids include serine, threonine, cysteine, tyrosine, asparagine, and glutamine; and aromatic amino acids include phenylalanine, tryptophan, and tyrosine.

Further, a variant may include deletion or addition of amino acids that have a minimal influence on properties and a secondary structure of a polypeptide. For example, a polypeptide may be conjugated to a signal (or leader) sequence at the N-terminus of a protein, which co-translationally or post-translationally directs transfer of the protein. In addition, the polypeptide may also be conjugated to another sequence or a linker for identification, purification, or synthesis of the polypeptide.

The "substitution with a different amino acid" is not limited as long as the substituted amino acid is different from that before substitution. That is, the "substitution with a different amino acid" is not limited as long as the $97^{th}$ amino acid from the N-terminus of an amino acid sequence of SEQ ID NO: 1 (i.e., alanine) is substituted with an amino acid other than alanine. Meanwhile, when it is expressed as "a particular amino acid is substituted" in the present invention, it is apparent that the amino acid is substituted with an amino acid different from the amino acid before the substitution, even if it is not specifically stated that the amino acid has been substituted with a different amino acid.

The protein variant may be a variant, in which the $97^{th}$ amino acid from the N-terminus of SEQ ID NO: 1 is substituted with any one amino acid selected from the group consisting of aspartic acid (D), glutamic acid (E), lysine (K), arginine (R), histidine (H), tyrosine (Y), asparagine (N), glutamine (Q), tryptophan (W), phenylalanine (F), methionine (M), and proline (P); specifically, a variant in which the $97^{th}$ residue from the N-terminus of SEQ ID NO: 1 is substituted with any one amino acid selected from aspartic acid (D), glutamic acid (E), lysine (K), arginine (R), and histidine (H), which are charged, large-sized amino acids; and more specifically, a variant in which the $97^{th}$ amino acid from the N-terminus of SEQ ID NO: 1 is substituted with glutamic acid (E).

The protein variant in which the $97^{th}$ amino acid from the N-terminus of SEQ ID NO: 1 is substituted with a different amino acid may also include a protein variant, in which the amino acid at the position corresponding to the $97^{th}$ position above is substituted with a different amino acid.

Additionally, it is apparent that any protein having an amino acid sequence with deletion, modification, substitution, or addition in part of the sequence, other than the $97^{th}$ position, can also be included within the scope of the present invention, as long as the amino acid sequence shows an activity corresponding to that of the protein variant described above.

Specifically, the protein variant of the present invention may include a polypeptide which has a homology or identity to the amino acid sequence of SEQ ID NOS: 3 of at least 80%, 90%, 95%, 96%, 97%, 98%, or 99%. Additionally, it is apparent that any protein, which has an amino acid sequence with deletion, modification, substitution, or addition in part of the sequence, can also be included within the scope of the present invention, as long as the protein has any of the above homologies or identities and shows an effect corresponding to the protein described above.

As used herein, the term "homology" or "identity" refers to a degree of relevance between two given amino acid sequences or nucleotide sequences and it may be expressed as a percentage. These terms "homology" and "identity" may often be used interchangeably.

Sequence homology or identity of conserved polynucleotides or polypeptides can be determined by standard alignment algorithm, and default gap penalties established by a program being used may be used together. Actually, homologous or identical sequences may generally hybridize with each other along the entire sequence or at least about 50%, 60%, 70%, 80%, or 90% of the entire length under moderate or highly stringent conditions. In hybridization, polynucleotides including a degenerate codon instead of a codon are also considered.

Whether any two polynucleotide- or polypeptide sequences have a homology, similarity, or identity can be determined using computer algorithms known in the art, e.g., "FASTA" program using default parameters introduced by Pearson et al. (1988) [*Proc. Natl. Acad. Sci. USA* 85: 2444]. Alternatively, Needleman-Wunsch algorithm (1970, *J. Mol. Biol.* 48: 443-453) performed in a Needleman program of The European Molecular Biology Open Software Suite of EMBOSS package (Rice et al., 2000, *Trends Genet.* 16: 276-277) (version 5.0.0 or a later version) may be used to determine the same (including GCG program package (Devereux, J., et al., *Nucleic Acids Research* 12: 387 (1984)), BLASTP, BLASTN, FASTA (Atschul, [S.] [F.,] [ET AL., *J MOLEC BIOL* 215]: 403 (1990); Guide to Huge Computers, Martin J. Bishop, [ED.,] Academic Press, San Diego, 1994, and [CARILLO ETA/.](1988) SIAM *J Applied Math* 48: 1073). For example, the homology, similarity, or identity can be determined using BLAST from the National Center for Biotechnology Information database or ClustalW.

The homology, similarity, or identity between polynucleotides or polypeptides may be determined, for example, by comparing the given sequence information using a GAP computer program, such as a program introduced by Needleman et al. (*J Mol Biol.* 48: 443 (1970)), as disclosed by Smith and Waterman (*Adv. Appl. Math* (1981) 2: 482). In brief, the GAP program defines a homology, similarity, or identity as the number of similar aligned symbols (i.e., nucleotides or amino acids) divided by the total number of the symbols in a shorter one of the two sequences. The default parameters for the GAP program may include: (1) a binary comparison matrix (including a value 1 for identity and a value 0 for non-identity) and the weighted comparison matrix of Gribskov, et al., (*Nucl. Acids Res.* 14: 6745 (1986)) as described by Schwartz and Dayhoff, eds. (Atlas Of Protein Sequence And Structure, National Biomedical Research Foundation, pp. 353-358 (1979) or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps.

Additionally, whether any two polynucleotide- or polypeptide sequences have a homology, similarity, or identity can be confirmed by comparing these sequences by southern hybridization experiments to be performed under defined stringent conditions, and the appropriate hybridization conditions to be defined may be determined within the scope of the art and by a method well known to those skilled in the art (e.g., J. Sambrook et al., *Molecular Cloning, A Laboratory Manual,* 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York).

Still another aspect of the present invention provides a polynucleotide which encodes the protein variant described above.

As used herein, the term "polynucleotide" refers to a DNA or RNA strand having more than a certain length as a nucleotide polymer, which is a long chain of nucleotide monomers connected by a covalent bond, and more specifically refers to a polynucleotide fragment encoding the protein variant described above.

In the present invention, the gene, which encodes the amino acid sequence of SEQ ID NO: 1 having the activity of carbon monoxide dehydrogenase (CODH), may be an acsA gene, and specifically may include a sequence containing the nucleotide sequence of SEQ ID NO: 2, but the gene is not limited thereto.

Considering codon degeneracy or the codons preferred in a bioorganism where the polypeptide is to be expressed, various modifications may be performed in the coding region of the polynucleotide encoding the protein variant of the present invention within the scope not altering the amino acid sequence of the polypeptide. Specifically, any polynucleotide sequence encoding a protein variant, in which the $97^{th}$ amino acid in the amino acid sequence of SEQ ID NO: 1 is substituted with a different amino acid, can be included without limitation.

Additionally, any sequence which encodes a protein variant, in which the $97^{th}$ amino acid of SEQ ID NO: 1 is substituted with a different amino acid, by hybridizing with any probe that can be prepared from known gene sequences (e.g., complementary sequences to all or part of the above polynucleotide sequence) under stringent conditions, can be included without limitation.

The term "stringent conditions" refers to conditions which enables specific hybridization between polynucleotides. Such conditions are specifically described in references (e.g., J Sambrook et al., supra). Hybridization requires that two polynucleotides include complementary sequences, although mismatches between bases are possible depending on the stringency of the hybridization. The term "complementary" is used to describe the relationship between mutually-hybridizable nucleotide bases. For example, with respect to DNA, adenine is complementary to thymine, and cytosine is complementary to guanine. Accordingly, the present invention may also include isolated polynucleotide fragments complementary to the entire sequence as well as substantially similar polynucleotide sequences. The stringency suitable for the hybridization of polynucleotides depends on the length and degree of complementarity of the polynucleotides, and the variables are well known in the art.

The polynucleotide encoding the protein variant of the present invention may be a polynucleotide wherein the $290^{th}$ nucleotide in the nucleotide sequence of SEQ ID NO: 2, cytosine (C), is substituted with a different nucleotide; specifically a polynucleotide wherein the $290^{th}$ nucleotide in the nucleotide sequence of SEQ ID NO: 2, cytosine (C), is substituted with adenine (A); and more specifically a polynucleotide consisting of the nucleotide sequence of SEQ ID NO: 4, but the polynucleotide is not limited thereto.

Still another aspect of the present invention provides a vector which includes a polynucleotide encoding the protein variant described above.

As used herein, the term "vector" refers to a DNA construct including a nucleotide sequence of a polynucleotide encoding a target protein, which is operably linked to a suitable control sequence so that the target protein can be expressed in a suitable host. The control sequence may include a promoter capable of initiating transcription, any operator sequence for controlling the transcription, a sequence encoding an appropriate mRNA ribosome-binding site, and a sequence for controlling the termination of transcription and translation. The vector, after being transformed into a suitable host cell, may be replicated or function irrespective of the host genome, or may be integrated into the genome itself.

The vector used in the present invention is not particularly limited, but any vector known in the art may be used. Examples of vectors conventionally used may include a natural or recombinant plasmid, cosmid, virus, and bacteriophage. For example, pWE15, M13, MBL3, MBL4, IXII, ASHII, APII, t10, t11, Charon4A, Charon21A, etc. may be used as a phage vector or cosmid vector; and those based on pBR, pUC, pBluescriptII, pGEM, pTZ, pCL, pET, etc. may be used as a plasmid vector. Specifically, vectors such as pDZ, pACYC177, pACYC184, pCL, pECCG117, pUC19, pBR322, pMW118, pCC1BAC, etc. may be used.

For example, the polynucleotide encoding a target protein in the chromosome may be replaced with a mutated polynucleotide through a vector for intracellular chromosomal insertion. The insertion of a polynucleotide into the chromosome may be performed using any method known in the art (e.g., homologous recombination), but the method is not limited thereto. The polynucleotide may further include a selection marker for confirming its successful insertion into the chromosome. A selection marker is used for selection of cells transformed with the vector, i.e., to confirm whether the target nucleic acid molecule has been inserted, and markers which confer selectable phenotypes (e.g., drug resistance, auxotrophy, resistance to cytotoxic agents, expression of surface proteins, etc.) may be used. Under the circumstances where selective agents are treated, only the cells capable of expressing the selection markers can survive or express other phenotypic traits, thereby enabling easy selection of the transformed cells.

Still another aspect of the present invention provides a microorganism which includes the protein variant.

In the present invention, the microorganism may be an acetogen. The term "acetogen" refers to a group of microorganisms that produce acetic acid through anaerobic metabolism using syngas or sugar as carbon and energy sources. The acetogen may be a microorganism which can perform the Wood-Ljungdahl pathway or can convert CO, $CO_2$, and/or $H_2$ to acetate. The microorganism includes all of the microorganisms in which a natural or artificial genetic modification has occurred, and it may be a microorganism in which a particular mechanism has been weakened or enhanced due to the insertion of a foreign gene, enhancement or inactivation of the activity of an endogenous gene, etc. In addition, the microorganism may be a microorganism in which a genetic mutation is introduced or an activity is enhanced according to the purpose.

For example, the microorganism may be *Acetoanaerobiumnotera* (ATCC 35199), *Acetonemalongum* (DSM 6540), *Acetobacterium carbinolicum* (DSM 2925), *Acetobacterium malicum* (DSM 4132), *Acetobacterium* sp. No. 446 (Morinaga et al., 1990, *J. Biotechnol.*, Vol. 14, p. 187-194), *Acetobacteriumwieringae* (DSM 1911), *Acetobacterium woodii* (DSM 1030), *Alkalibaculumbacchi* (DSM 22112), *Archaeoglobusfulgidus* (DSM 4304), *Blautiaproducta* (DSM 2950, previously *Ruminococcus productus*), previously *Peptostreptococcus productus*), *Butyribacterium methylotrophicum* (DSM 3468), *Clostridium aceticum* (DSM 1496), *Clostridium autoethanogenum* (DSM 10061, DSM 19630, and DSM 23693), *Clostridium carboxidivorans* (DSM 15243), *Clostridium coskatii* (ATCC No. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2 (ATCC 55380), *Clostridium ljungdahlii* O-52 (ATCC 55989), *Clostridium mayombei* (DSM 6539), *Clostridium methoxybenzovorans* (DSM 12182), *Clostridium ragsdalei* (DSM 15248), *Clostridium scatologenes* (DSM 757), *Clostridium* sp. ATCC 29797 (Schmidt et al., 1986, *Chem. Eng. Commun.*, Vol. 45, p. 61-73), *Desulfotomaculum kuznetsovii* (DSM 6115), *Desulfotomaculum thermobezoicum* subsp. *thermosyntrophicum* (DSM 14055), *Eubacteriumlimosum*, *Methanosarcina acetivorans* C2A (DSM 2834), *Moorella* sp. HUC22-1 (Sakai et al., 2004, *Biotechnol. Let.*, Vol. 29, p. 1607-1612), *Moorella thermoacetica* (DSM 521, previously *Clostridium thermoaceticum*), *Moorella thermoautotrophica* (DSM 1974), *Oxobacterpfennigii* (DSM 322), *Sporomusaaerivorans* (DSM 13326), *Sporomusa ovata* (DSM 2662), *Sporomusa silvacetica* (DSM 10669), *Sporomusasphaeroides* (DSM 2875), *Sporomusatermitida* (DSM 4440), *Thermoanaerobacter kivui*, etc. Specifically, the microorganism may be one selected from the group consisting of *Acetobacterium woodii*, *Thermoanaerobacter kivui*, and *Eubacterium limosum*, and more specifically *Eubacterium limosum*.

The protein variant of the present invention may be one which can enhance the CO availability of the microorganism including the same, and the microorganism may be one in which the CO availability is enhanced compared to a microorganism which does not include the protein variant of the present invention.

As used herein, the term "enhanced carbon monoxide (CO) availability" includes the meanings of "an increase in the ability of fixing carbon monoxide (CO)", "an increase of resistance to carbon monoxide (CO)", etc. In the presence of carbon monoxide in a culture environment, the enhanced carbon monoxide (CO) availability may appear in phenotypes, such as exhibition of a higher growth rate compared to a natural microorganism, production of a large amount of metabolites, etc.

In an embodiment of the present invention, the microorganism of the present invention may be *Eubacterium limosum* deposited under Accession No. KCTC 14201BP, but the microorganism is not limited thereto.

The microorganism of the present invention may be a microorganism in which a CODH nickel insertion accessory protein is further inactivated.

The inactivation may be achieved by the application of various kinds of methods known in the art. Examples of the methods include: 1) a method of deleting all or part of the gene encoding the protein; 2) a method of modifying the expression control sequence so as to reduce the expression of the gene encoding the protein; 3) a method of modifying the sequence of the gene encoding the protein so as to remove or weaken the activity of the protein; 4) a method of introducing an antisense oligonucleotide (e.g., antisense RNA) which binds complementarily to a transcript of the gene encoding the protein; 5) a method of making the attachment of a ribosome impossible by forming a secondary structure by adding a sequence, which is complementary to the Shine-Dalgarno (SD) sequence, on a front end of the SD sequence of the gene encoding the protein; 6) a method of reverse transcription engineering (RTE), in which a reversely-transcribed promoter is added to the 3' terminus of the open reading frame (ORF) of the polynucleotide sequence of the gene encoding the protein, etc.; and the inactivation may be achieved by a combination of these methods, but the methods are not particularly limited thereto.

Specifically, the protein inactivation may be a modification of the gene sequence encoding a protein so that the activity of the protein is removed or weakened, and more specifically, it may be an inactivation of a protein due to a frame shift mutation by insertion of a nucleotide(s) within the polynucleotide sequence encoding the protein, but the protein inactivation is not limited thereto.

In an embodiment of the present invention, the microorganism may be one which includes a protein variant in which the $97^{th}$ residue from the N-terminus of SEQ ID NO: 1, alanine (A), is substituted with a different amino acid, and further includes any one or more mutations among the mutations described in Table 1 below.

TABLE 1

| Locus tag | Gene | Mutation (Type) | AA change | Description |
|---|---|---|---|---|
| ELIM_c1031 | — | —356T (insertion) | Asn119Lys | Integrase family protein |
| ELIM_c1038 | — | G133A (SNV) | Glu48Lys | Putative ATPase, transposase-like protein |
| ELIM_c1073 | dam | T408G (SNV) | Tyr136X133 | N6 adenine-specific DNA methylase D12 class |
| ELIM_c1654 | cooC2 | —216A (insertion) | Ala72fsX92 | CODH nickel insertion accessory protein |

In another embodiment of the present invention, the microorganism of the present invention may be one which includes a protein variant in which the 97$^{th}$ residue from the N-terminus of SEQ ID NO: 1, alanine (A), is substituted with a different amino acid, and further includes any one or more mutations among the mutations described in Table 2 below.

TABLE 2

| Samples | Locus tag | Position | Type | Reference | Allele | AA change |
|---|---|---|---|---|---|---|
| ECO_acs | ELIM_c1653 | 1,832,907 | SNV | C | T | Ala$^{92}$Val |
| A, 2, 3, 4 | | 1,832,922 | SNV | C | A | Ala$^{97}$Glu |
| 1, 2, 3, 4 | ELIM_c1031 | 1,126,411 | Insertion | — | T | Asn$^{119}$LysfsX132 |
| 1, 2, 3, 4 | Intergenic | 1,970,647 | SNV | G | A | — |
| 1, 2, 3 | ELIM_c1654 | 1,834,784 | Insertion | — | A | Ala$^{72}$AlafsX92 |
| 1, 2, 3 | ELIM_c3581 | 3,896,831 | SNV | C | A | Asp$^{66}$Tyr |
| 1, 2, 3 | Intergenic | 1,972,135 | SNV | T | C | — |
| 1, 2, 4 | ELIM_c1038 | 1,130,590 | SNV | G | A | Glu$^{48}$Lys |
| 1, 2, 4 | ELIM_c1073 | 1,159,055 | SNV | T | G | Tyr$^{136}$X |
| 1, 4 | ELIM_c0527 | 588,552 | Deletion | C | — | Gly$^{279}$ValfsX282 |
| 1 | ELIM_c0236 | 256,802 | SNV | G | T | Ser$^{348}$X |
| 1 | ELIM_c0337 | 370,333 | SNV | C | G | Glu$^{315}$Gln |
| 1 | ELIM_c0437 | 483,053 | SNV | G | A | Ala$^{185}$Val |
| 1 | ELIM_c0530 | 592,464 | SNV | G | A | Ile$^{774}$Ile |
| 1 | | 726,708 | SNV | G | C | Pro$^{74}$Arg |
| | ELIM_c0659 | 726,714 | SNV | T | C | Asp$^{72}$Gly |
| 1 | ELIM_c0672 | 739,966 | SNV | C | A | Ala$^{88}$Ser |
| 1 | ELIM_c0750 | 832,772 | SNV | G | C | Ala$^{326}$Ala |
| 1 | ELIM_c0854 | 938,560 | SNV | A | G | Lys$^{490}$Arg |
| 1 | ELIM_c0866 | 952,049 | SNV | G | A | Val$^{789}$Val |
| 1 | ELIM_c1063 | 1,148,482 | SNV | G | T | Gly$^{741}$Trp |
| 1 | ELIM_c1325 | 1,436,020 | SNV | A | G | Ile$^{865}$Thr |
| 1 | ELIM_c2814 | 3,101,419 | SNV | C | A | Ala$^{63}$Ala |
| 1 | ELIM_c2882 | 3,162,881 | SNV | G | A | Gly$^{38}$Arg |
| 1 | ELIM_c2942 | 3,240,199 | SNV | C | A | Arg$^{143}$Arg |
| 1 | ELIM_c3150 | 3,443,977 | SNV | T | C | Asp$^{310}$Gly |
| 1 | ELIM_c3386 | 3,699,117 | SNV | T | A | Leu$^{144}$X |
| 1 | ELIM_c3427 | 3,747,388 | SNV | G | T | Asp$^{56}$Tyr |
| 1 | ELIM_c3691 | 3,999,914 | SNV | C | A | Met$^{194}$Ile |
| 1 | Intergenic | 3,309,964 | SNV | A | T | — |
| 2 | ELIM_c2071 | 2,255,729 | SNV | C | A | Gly$^{14}$Val |
| 2 | ELIM_c2621 | 2,852,312 | SNV | G | C | Leu$^{152}$Leu |
| 2 | ELIM_c3002 | 3,306,141 | SNV | C | T | Ser$^{47}$Ser |
| 2 | Intergenic | 3,183,238 | SNV | G | C | — |
| 2 | Intergenic | 3,305,753 | SNV | G | A | — |
| 3 | ELIM_c0293 | 322,696 | SNV | G | T | Ile1$^{70}$Ile |
| 4 | ELIM_c0006 | 5,401 | SNV | G | T | His$^{99}$Asn |
| 4 | ELIM_c1330 | 1,446,536 | SNV | G | A | Val$^{392}$Val |
| 4 | Intergenic | 1,946,081 | SNV | G | C | — |

In another embodiment of the present invention, the microorganism of the present invention may be one which includes a protein variant in which the $97^{th}$ residue from the N-terminus of SEQ ID NO: 1, alanine (A), is substituted with a different amino acid, and further includes any one or more mutations among the mutations described in Table 3 below.

TABLE 3

| Locus tag | Gene | Mutation (Type) | AA change | Description |
|---|---|---|---|---|
| ELIM_c0006 | — | G1265T (SNV) | Ala$^{422}$Glu | Gp11 |
| ELIM_c2214 | — | —413G (insertion) | Arg$^{138}$Arg | Hypothetical protein |
| ELIM_c2227 | — | G82T (SNV) | Ala$^{28}$Ser | Terminase |
| ELIM_c1653 | acsA | C290A (SNV) | Ala$^{97}$Glu | CODH catalytic subunit |
| Intergenic | — | C2393145— (deletion) | — | — |
|  | — | A2393154— (deletion) | — | — |

Still another aspect of the present invention provides a method for preparing a compound, which includes a step of culturing the microorganism of the present invention.

The microorganism may be an acetogen, which is the same as described above.

In the present invention, the term "culturing" refers to growing the microorganism in an appropriately adjusted environment. The culturing process of the present invention may be performed according to the appropriate medium and conditions for culture known in the art. The culturing process may easily be adjusted for use by one of ordinary skill in the art according to the strain to be selected. Specifically, the culture may be a batch culture, a continuous culture, and a fetch culture, but the culture is not limited thereto. The culturing not only includes a process of growing an acetogenic microorganism in a culture medium, but also includes a process of anabolism, catabolism, or conversion of a substrate provided in the culture medium although the cells may not grow.

As used herein, the term "medium" refers to a mixture of materials which contains nutrient materials required for the culturing of the microorganism as a main ingredient, and it supplies nutrient materials, growth factors, etc. along with water that is essential for survival and growth. Specifically, as the medium and other culture conditions used for culturing the microorganism of the present invention, any medium used for conventional culture of an acetogenic microorganism may be used without particular limitation. Additionally, the microorganism of the present invention may be cultured under anaerobic conditions in a conventional medium containing an appropriate carbon source, nitrogen source, phosphorus source, inorganic compound, amino acid, and/or vitamin, etc. while adjusting temperature, pH, etc. In an embodiment of the present invention, the carbon source may be a syngas (e.g., CO and $CO_2$), and specifically CO, but the carbon source is not limited thereto.

Additionally, in the process of culturing the microorganism of the present invention, a syngas, which contains gases such as $H_2$ in addition to CO and $CO_2$, may be supplied. The syngas may further contain $N_2$, but the syngas is not limited thereto. The syngas may be a mixed gas consisting of carbon monoxide (CO), carbon dioxide ($CO_2$), and hydrogen ($H_2$), which are obtained through a gasification process of various carbon-based raw materials (e.g., waste, coal, coke, lower hydrocarbon gas, naphtha, heavy oil, etc.), but the syngas is not limited thereto.

In the preparation method above, the microorganism may be a microorganism having the ability to produce the compound of the present invention. However, the preparation method is not limited thereto, and the microorganism may be a microorganism into which a gene encoding an enzyme involved in compound synthesis is further introduced.

In an embodiment, the compound may be acetoin.

In an embodiment of the present invention, a microorganism including a protein variant, wherein the $97^{th}$ residue in the amino acid sequence of SEQ ID NO: 1 is substituted with a different amino acid, was further introduced with an alsS gene derived from *Bacillus subtilis* and an alsD gene derived from *Aeromonas hydrophila*, that are necessary for acetoin synthesis, and thereby the acetoin synthesis in the resulting microorganism was confirmed.

Still another aspect of the present invention provides a method for preparing a microorganism with enhanced carbon monoxide (CO) availability, which comprises a step of culturing the microorganism under a gas condition comprising carbon monoxide (CO).

The microorganism may be an acetogen, which is the same as described above.

The gas condition may be a condition in which CO is contained in an amount of 20% to 50% relative to the total gas composition, and specifically, a syngas condition in which CO, $CO_2$, $H_2$, and $N_2$ are contained. The composition ratio of the syngas may be 44% of CO, 22% of $CO_2$, 2% of $H_2$, and 32% of $N_2$, but the composition ratio of the syngas is not limited thereto, and may be used after appropriate adjustment under conditions that do not limit the growth of microorganisms.

Specifically, the culturing step in the preparation method above may be a process of adaptive laboratory evolution (ALE). The ALE is a method used for obtaining a mutation in a microorganism, in which appropriate stress is applied during the growth of a microorganism thereby causing changes in the genotype and phenotype of the microorganism.

In an embodiment of the present invention, a strain was cultured under the condition of a syngas comprising 44% of CO, 22% of $CO_2$, 2% of $H_2$, and 32% of $N_2$, and thereby, a microorganism with enhanced CO availability was prepared.

The microorganism with enhanced CO availability prepared by the preparation method above may be a microorganism, which comprises a protein variant having an activity of carbon monoxide dehydrogenase (CODH); specifically, a microorganism which comprises a protein variant wherein the $97^{th}$ amino acid of SEQ ID NO: 1 is substituted with a different amino acid; and more specifically, a microorganism which is *Eubacterium limosum* deposited under Accession No. KCTC 14201BP, but the microorganism is not limited thereto.

Advantageous Effects

The microorganism, which comprises the protein variant of the present invention, is a microorganism that shows enhanced CO availability under autotrophic conditions, and the microorganism has an excellent ability to produce metabolites using CO contained in waste gas and can maintain a high growth rate. Therefore, the variant of the present invention and the microorganism comprising the same can be applied to a method for producing compounds and effectively used as a carbon resource technology.

DETAILED DESCRIPTION OF THE INVENTION

Figures 1A, 1B, 1C, 1D:
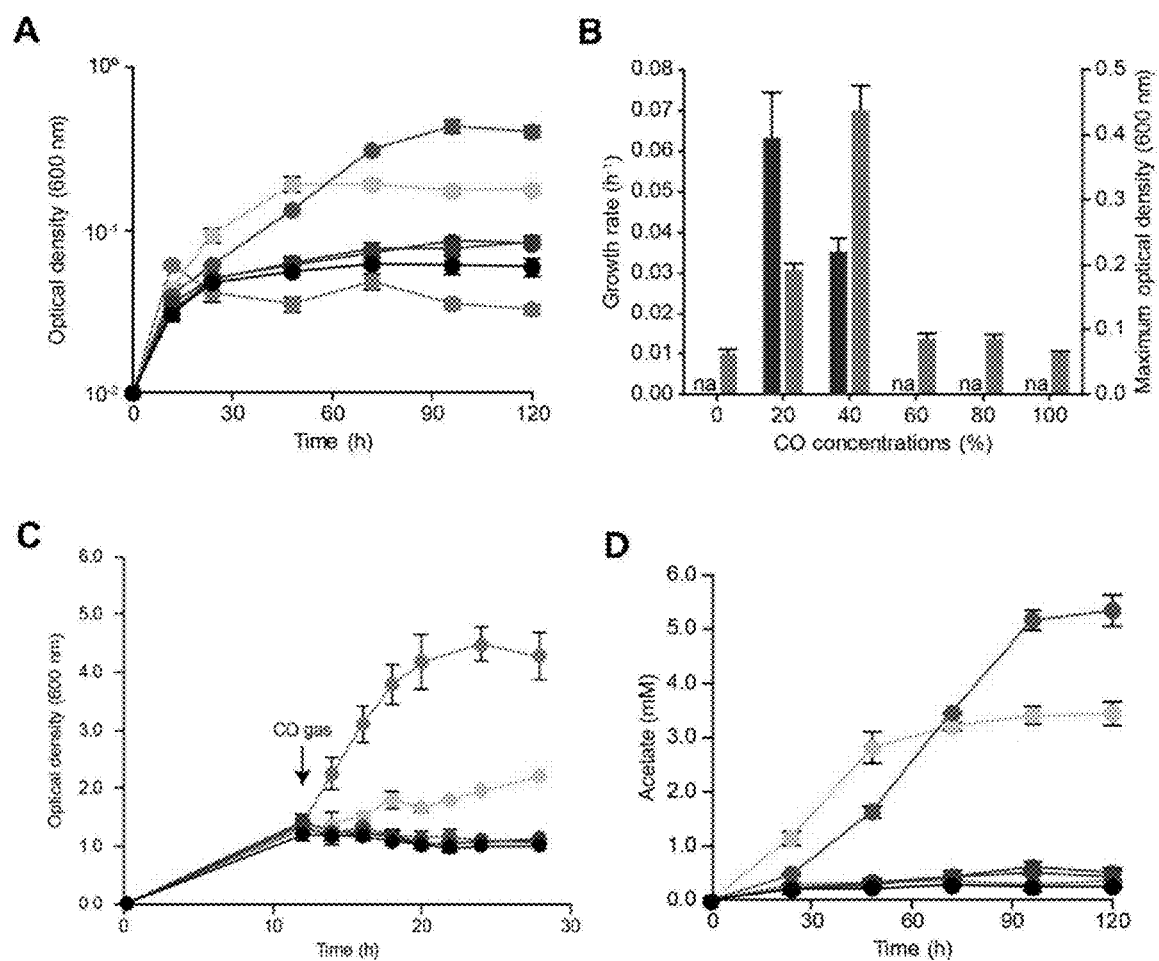
FIGS. 1A-1D show graphs confirming the cell densities ($OD_{600}$) and the growth rate of E. limosum according to CO concentrations during culture (FIGS. 1A and 1B), growth inhibition by CO treatment (FIG. 1C), and a production level of a metabolite (acetate) of E. limosum according to CO concentrations during culture (FIG. 1D), respectively (in which "na" denotes "not available").

Hereinafter, the present invention will be described in more detail with reference to the following Examples. However, these Examples and Experimental Examples are for illustrative purposes only and the scope of the invention is not limited by these Examples and Experimental Examples.

EXAMPLE 1

Materials and Methods 1.1 Strains and Culturing Conditions

Eubacterium limosum ATCC 8486 was distributed by the Leibniz Institute DSMZ-German Collection of Microorganisms and Cell Cultures (DSMZ, Braunschweig, Germany) and used. The strain was cultured under anaerobic conditions at 37° C. As the culture medium, DSMZ 135 was used after modification and the specific composition is as follows: 1 g/L ammonium chloride, 2 g/L yeast extract, 10 g/L sodium bicarbonate, 0.1 g/L magnesium sulfate heptahydrate, 0.3 g/L cysteine-HCl, 10 mL vitamin solution (4 mg/L biotin, 4 mg/L folic acid, 20 mg/L pyridoxine-HCl, 10 mg/L thiamine-HCl, 10 mg/L riboflavin, 10 mg/L nicotinic acid, 10 mg/L pantothenate, 0.2 mg/L vitamin B12, 10 mg/L p-aminobenzoic acid and 10 mg/L lipoic acid), 4.64 mM $KH_2PO_4$, 5.36 mM $K_2HPO_4$, 4 μM resazurin, and 20 mL trace element solution (1.0 g/L nitrilotriacetic acid, 3.0 g/L $MgSO_4.7 H_2O$, 0.5 g/L $MnSO_4.H_2O$, 1.0 g/L NaCl, 0.1 g/L $FeSO_4.7 H_2O$, 180 mg/L $CoSO_4.7 H_2O$, 0.1 g/L $CaCl_2.2 H_2O$, 180 mg/L $ZnSO_4.7 H_2O$, 10 mg/L $CuSO_4.5 H_2O$, 20 mg/L $KAl(SO_4)_2.12 H_2O$, 10 mg/L $H_3BO_3$, 10 mg/L $Na_2MO_4.2 H_2O$, 30 mg/L $NiCl_2.6 H_2O$, 0.3 mg/L $Na_2SeO_3.5 H_2O$, 0.4 mg/L $Na_2WO_4.2 H_2O$). The strain was cultured under the conditions of 50 mL headspace 200 kPa filled with 0%, 20%, 40%, 60%, 80%, and 100% CO using 100%, 80%, 60%, 40%, 20%, and 0% $N_2$, respectively.

In order to increase the autotrophic growth rate during the process of adaptive evolution, 40 mM NaCl conjugated with sodium dependent ATP synthase was supplemented to the medium.

1.2 Adaptive Laboratory Evolution (ALE)

The ALE experiment was performed under the syngas conditions (44% CO, 22% $CO_2$, 2% $H_2$, and 32% $N_2$) described in Example 1.1 above. Before performing the ALE, a pre-adaptation step was performed by allowing the syngas to pass therethrough three times in the mid-exponential phase. The ALE was performed with respect to four independent populations, and the medium in the mid-exponential phase was transferred to a fresh medium while performing the ALE.

1.3 Whole Genome Sequencing Library

In order to construct a DNA library for entire genome re-sequencing, genomic DNA samples were extracted from an evolved population. Cell stock was cultured in a glucose (5 g/L) culture medium at 37° C. for 12 hours. The cells were collected and resuspended in 500 μL of a lysis buffer containing Tris-Cl (pH 7.5), 5 M NaCl, 1 M $MgCl_2$, and 20% Triton X-100. Then, cells were frozen using liquid nitrogen and crushed using a mortar. The crushed powders were resuspended in 600 μL of a nuclei lysis solution (Promega, Madison, Wis.), incubated at 80° C., and cooled to 4° C. RNA was removed from the cell lysate using an RNase A solution. The proteins in the lysate were precipitated using a protein precipitation buffer (Promega). After precipitation, the sample was cooled at 4° C. for 10 minutes and centrifuged at 16,000×g for 10 minutes. The supernatant was transferred to a new tube and 1× volume of isopropanol was added thereto. The mixture was centrifuged at 16,000×g for 5 minutes to obtain a DNA pellet, which was washed twice with 80% ethanol. The quality of the DNA obtained was determined by the A260/A280 ratio (>1.9) and tested by gel electrophoresis, and the concentration was quantified using a Qubit® 2.0 Fluorometer (Invitrogen, Carlsbad, Calif.) with a Qubit™ dsDNA HS Assay kit (Invitrogen). The sequencing library was constructed using a TruSeq Nano DNA library prep kit (Illumina, La Jolla, Calif.). The constructed library of the evolved population was sequenced using an Illumina Hiseq2500 (a rapid-run mode as a 50 cycle-ended reaction), and the constructed library of the isolated clone was sequenced with an Illumina MiSeq (a 150-cycle ended reaction).

1.4 Screening of Mutations

Sequencing readings were performed with the CLC genomics Workbench v6.5.1 (CLC bio, Aarhus, Denmark). Adapter sequences were removed with a trimming tool having default values (quality limit and ambiguous nucleotides residues 2).

variation detection tool with the following parameters: neighborhood radius: 5, maximum gap and mismatch count: 5, minimum neighborhood quality: 30, minimum central quality: 30, minimum coverage: 10, minimum variant frequency: 10%, maximum expected alleles: 4, non-specific matches: ignore and genetic code: bacterial and plant plastid.

1.5 Isolation of Single Clones from Evolved Population

The evolved population was streaked on an RCM agar medium to isolate single clones. In order to confirm the sequence of each mutation site, PCR was performed using the primer pairs shown in Table 4, and thereby, the genomic region was amplified and the sequences were analyzed by Sanger sequencing.

TABLE 4

| Primer | Sequence (5' → 3') | Note |
|---|---|---|
| c1031_mut_confirm_F | CAAAAGCCCTTAAA TAGGCG (SEQ ID NO: 5) | For amplification of ELIM_c1031 region containing mutation site (577 bp) and sequencing of the mutation site using only forward primer |
| c1031_mut_confirm_R | AATGTCAAGCTGTA TTTGCG (SEQ ID NO: 6) | |
| c1073_mut_confirm_F | GTGTCTGGCAAATG GTATTG (SEQ ID NO: 7) | For amplification of ELIM_c1031 region containing mutation site (968 bp) and sequencing of the mutation site using only forward primer |
| c1073_mut_confirm_R | TTTAATCACGGTAT CACCCC (SEQ ID NO: 8) | |
| c1038_mut_confirm_F | GTGTGAACATTGCA CAGTC (SEQ ID NO: 9) | For amplification of ELIM_c1031 region containing mutation site (945 bp) and sequencing of the mutation site using only forward primer |
| c1038_mut_confirm_R | CAATCTCTGGAAAA AGCTGC (SEQ ID NO: 10) | |
| Final_confirm_foracsA_HA_F | ACTGGCACTTGACA CCGC (SEQ ID NO: 11) | For amplification of ELIM_c1031 region containing mutation site (3,976 bp) |
| Final_confirm_forcooC2_HA_R | ATAACAGCAACACC TGGG (SEQ ID NO: 12) | |
| acsA_mut_confirm_F | ATGCAGACTCCGTT CTGG (SEQ ID NO: 13) | For sequencing of mutation site in acsA |
| cooc2_mut_confirm_F | GTTAAAGAATGGAC TGGC (SEQ ID NO: 14) | For sequencing of mutation site in cooC2 |

The resulting readings were mapped into *E. limosum* ATCC 8486 reference genome (NCBI Accession No. NZ_CP019962.1) using mapping parameters (mismatch cost: 2, indel cost: 3, deletion cost: 3, length fraction: 0.9, similarity fraction: 0.9). Variation detection from the mapped reading values was performed using a quality-based The selected single clones containing a mutation was cultured in a DSMZ 135 medium, to which CO was added to the headspace, and so as to measure the growth rate and the amounts of metabolites produced were measured.

1.6 Construction of Plasmid for Biosynthesis of Acetoin

The primers used are shown in Table 5 below.

TABLE 5

| Primer | Sequence (5' → 3') | Note |
|---|---|---|
| alsS_F | CCATACGCGTGGATCCCTCGAGATGTTGACAA AAGCAACAAAAGAACAAAAATC (SEQ ID NO: 15) | For amplification of alsS and cloning pJIR750_alsD_alsS |
| alsS_R | ATGATTACGAATTCGAGCTCCTAGAGAGCTTT CGTTTTCATGAGTTCC (SEQ ID NO: 16) | |

TABLE 5-continued

| Primer | Sequence (5' → 3') | Note |
|---|---|---|
| alsD_F | CGGTACCCGGGGATCCACGCGTATGGAAACT AATAGCTCGTGCGATTG (SEQ ID NO: 17) | For amplification of alsD and cloning pJIR750_alsD |
| alsD_R | ATGCCTGCAGGTCGACCTAACCCTCAGCCGCA CGGATAG (SEQ ID NO: 18) | |
| alsD_P1121_U1121_F | ACATCTCGAGGGATCCCATTTACCGGGCCAAG C (SEQ ID NO: 19) | For cloning pJIR750_alsD_U1121_P1121_alsS |
| alsD_P_U1121_univ | TAGTTTCCATACGCGTTTCCTCCTTGAAACAA GACGTTCTGAG (SEQ ID NO: 20) | |
| alsS_P2885_U1121_F3 | CCGGTAAATGGGATCCTTTAAGCGTGAAGTG AAAAGAATGG (SEQ ID NO: 21) | For cloning pJIR750_alsD_U1_1121-P1121_P2885_U1121_alsS |
| alsS_P_U1121_univ | TTGTCAACATCTCGAGTTCCTCCTTGAAACAA GACGTTCTGAG (SEQ ID NO: 22) | |
| PU_confirm_F | CAGTTAAACGGCCGACTGCTTG (SEQ ID NO: 23) | For confirmation of transformant by PCR (902 bp) |
| PU_confirm_R | GTCCAGCCGGTTAAACGTGC (SEQ ID NO: 24) | |

The pJIR750ai plasmid was used as a shuttle vector, and the plasmid was cloned into *E. coli* DH5a (Enzynomics, Inc., Korea). The alsS gene (acetolactate synthase) was obtained from *Bacillus subtilis* and the alsD gene (acetolactate decarboxylase) was obtained from *Aeromonas hydrophila* by gene synthesis. The synthesized alsS and alsD genes were amplified using the alsS_F-alsS_R and alsD_F-alsD_R primers. PvuI-treated pJIR750ai (named pJIR750_PvuI_cut) was digested with BamHI and SalI, and the amplified alsD was assembled using an In-Fusion HD cloning Kit (TaKaRa, Japan). The assembled plasmid (pJIR_alsD) was linearized using SacI and BamHI, and then the pJIR750_alsS_alsD plasmid was prepared by assembling the alsS gene using the in-Fusion cloning. In order to control gene expression, the promoters of ELIM_c2885 (pyruvate:ferredoxin oxidaoreductase) and ELIM_c1121 ([Fe] hydrogenase), which are genes constitutively expressed at high levels in *E. limosum*, were selected and used. The wild-type promoter was amplified using genomic DNA of *E. limosum* and inserted into the pJIR750_alsS_alsD plasmid to construct the pJIR750_alsS_U_1121_P1121_P2885_U1121_alsD plasmid.

1.7 Transformation

A protocol for preparing electrocompetent cells was performed. The cells were cultured in 100 mL of a DSM 135 medium to which glucose (5 g/L) was added. In the early-exponential phase ($OD_{600}$: 0.3 to 0.5), the cells were recovered by centrifugation at 10,000 rpm at 4° C. for 10 minutes. The recovered cells were washed with 50 mL of a 270 mM sucrose buffer (pH 6) and resuspended to a final concentration of $10^{11}$ cells/mL.

The pJIR750_alsS_U_1121_P1121_P2885_U1121_alsD plasmid (1.5°μg to 2°μg) was added to the electrocompetent cells, and the resulting solution was transferred to a°0.1-cm-gap Gene Pulser cuvette (Bio-Rad, Hercules, Calif.). Then, a 2.0°kV pulse was applied to the cells and the cells were immediately resuspended in 0.9° mL of a reinforced clostridial medium (RCM). The cells were recovered on ice for 5° minutes and incubated at 37° C. for 16° hours. The recovered cells were plated on an RCM plate (1.5% agar) containing thiamphenicol (15°μg/mL). Single colonies were selected and cultured in a DSM 135 medium to which glucose (5 g/L) was added.

1.8 Measurement of Metabolites

The primary metabolite was measured by HPLC (Waters, Milford, Mass.). A refractive index detector and a MetaCarb 87 H 300° mm°×°7.8° mm column (Agilent, Santa Clara, Calif.) were used. As the mobile phase, a 0.007 N sulfuric acid solution was used at a flow rate of 0.6° mL/min. The oven temperature was 37° C. for acetate and butyrate and 50° C. for acetoin.

1.9 Measurement of Gas

The CO concentration was measured by gas chromatography (Shimadzu, Japan). A thermal conductivity detector and a ShinCarbon ST Micropaked column (1 mm×2 m, 1/16", 100/120 mesh) (Restek, Bellefonte, Pa.) were used. Helium was used as a carrier gas at a flow rate of 30 mL/min. The initial oven temperature was set at 30° C. for 1 minute, and the increase rate was 5° C./min until the temperature reached 100° C. The temperatures of the injector and the detector were both set at 100° C.

EXAMPLE 2

Results of Experiments 2.1 Growth of *E. limosum* ATCC 8486 in Carbon Monoxide (CO) Culture Conditions In order to confirm the CO tolerance of *E. limosum* ATCC 8486, cell growth was confirmed by culturing the strain in 100 mL of the modified DSMZ 135 medium of Example 1.1 at CO concentrations of 0%, 20%, 40%, 60%, 80%, and 100%, respectively. As a control group, the strain was incubated under 100% $N_2$ gas without CO. The results are shown in FIGS. 1A and 1B.

The control group showed a growth rate of 0.031±0.00211$^{-1}$ and a maximum cell density of 0.049±0.005 (FIG. 1A). This low cell growth rate was assumed to be due to the presence of sodium bicarbonate and a yeast extract in the medium. At the CO concentration of 20%, it was confirmed that the cell growth rate was 0.066±0.00211$^{-1}$ and the maximum cell density was 0.193±00.010. However, at the CO concentration of 40% to 100%, the cell growth rate was in the range of 0.058±0.000 h$^{-1}$ to 0.040±0.000 h$^{-1}$ and the maximum cell density was in the range of 0.438±0.038 to 0.063±0.003.

Compared to the control group, the cell growth rate was increased by 2.15-fold at the CO concentration of 20% (FIG. 1B). However, as the CO concentration increased, the cell growth rate gradually decreased to 1.29-fold (in a 100% CO condition). Cells grown at the highest CO concentration had a maximum cell density of less than 0.063, which is slightly higher compared to the maximum cell density in the control group. These results indicate that cell proliferation was inhibited by the increase of the CO concentration in the growth medium.

These results show a trend similar to the results that growth is completely inhibited when CO is present at a concentration of 25% or higher in the culture headspace in an experiment using an acetogen, *Acetobacterium woodii* (which is a strain close to the existing *E. limosum*); or to the results that growth is inhibited at CO concentrations of 50% or higher in an experiment culturing *Thermoanaerobacter kivui*. These results indicate that although an acetogenic microorganism can utilize CO to some extent, its growth is significantly affected by CO concentration.

In addition, experiments to confirm the effect of CO on cell growth were performed. First, in a DSMZ 135 medium containing glucose (5 g/L), the microorganism was cultured until it reached the mid-exponential phase. In the mid-exponential phase (an $OD_{600}$ value of 1.320), CO gas at concentrations of 0% (=100% $N_2$, control group), 20%, 40%, 60%, 80%, or 100% was injected at the same pressure. After 2 hours, the $OD_{600}$ value was measured. As a result, it was confirmed that the $OD_{600}$ value was decreased at all CO concentrations (FIG. 1C).

Then, in order to confirm the effect of CO on the phenotype, metabolites produced by *E. limosum* were analyzed and the results are shown in FIG. 1D. Among the identified metabolites, acetate was the most important metabolite, and acetate is known as a major metabolic final product of an acetogen under autotrophic culture conditions. Acetate biosynthesis produces ATP, which is required for cellular functions of an acetogen, and thus, acetate production is closely related to cell growth.

The amount of acetate produced by the cells cultured in the absence of CO was at the level of 0.384±0.017 mM. However, under the conditions of CO at concentrations of 20%, 40%, 60%, 80%, and 100%, the acetate production level was 3.457±0.226 mM, 5.363±0.283 mM, 0.618±0.107 mM, 0.519±0.030 mM, and 0.279±0.006 mM, respectively. It was confirmed that the amount of acetate produced was increased under the conditions of CO at concentrations of 20% and 40% compared to other conditions. In addition, it was confirmed that the acetate production pattern was dependent on cell growth. In conditions of high CO concentrations, the amount of acetate produced decreased as the CO concentration increased, but it was not a significant change compared to the control group (P-value>0.05).

These results suggest that acetate production correlates with a growth pattern that is affected by the amount of CO concentration in a culture medium, which suggests that the increase of CO tolerance potentially enhances acetate production in *E. limosum*.

2.2 ALE of *E. limosum* ATCC 8486 in CO Culture Conditions

In order to improve the CO tolerance of *E. limosum*, adaptive laboratory evolution (ALE) was applied.

First, the conditions to express desired phenotypes were set.

Figures 2A, 2B, 2C, 2D, 2E, 2F:
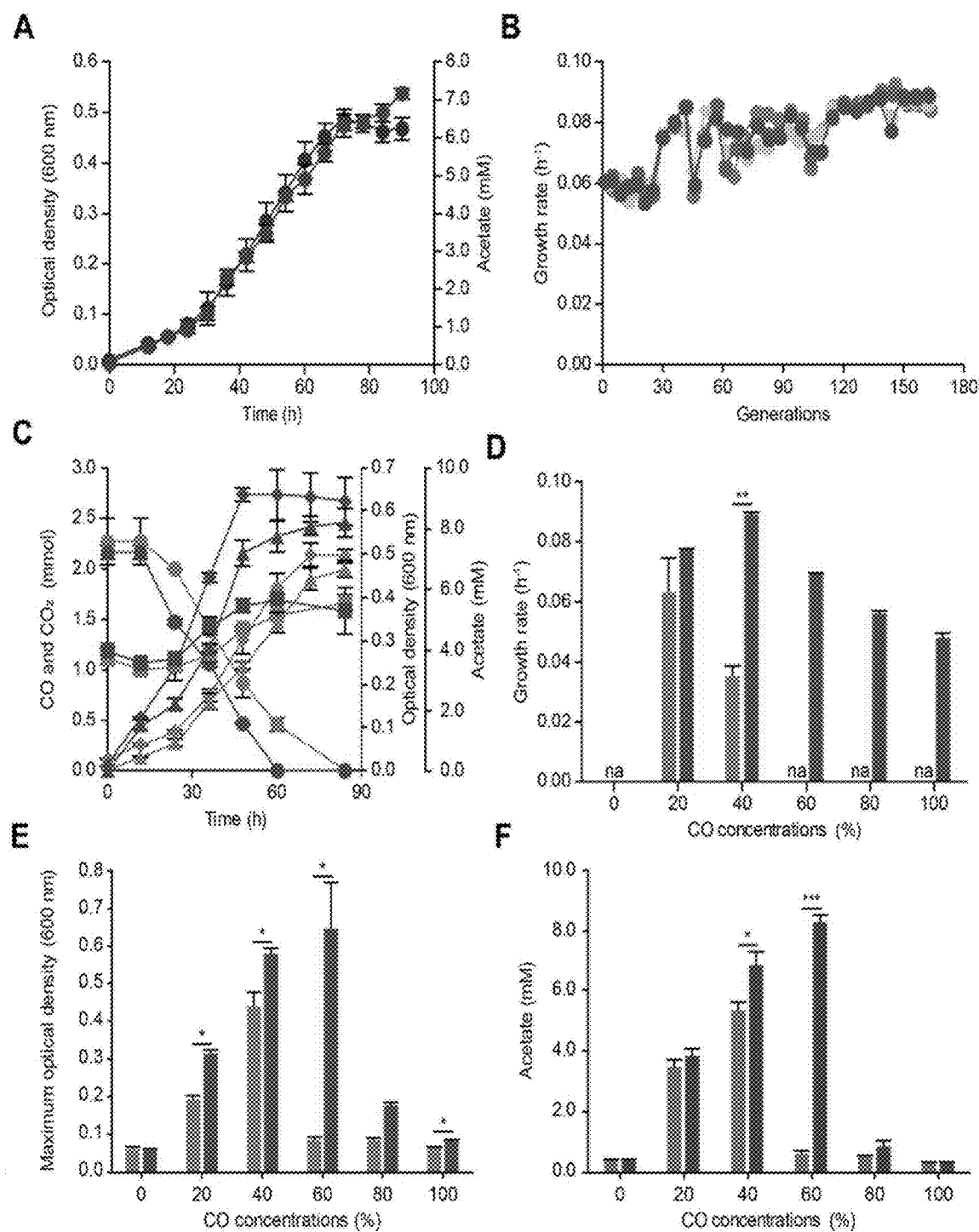
FIG. 2A shows a graph confirming a cell density and an acetate production level under culture conditions for determining the transfer point of ALE.
FIG. 2B shows a graph illustrating the measurement results of a cell growth rate according to evolution of generations during the process of ALE application.
FIG. 2C shows a graph confirming a profile with respect to the growth of an ECO strain and a parent strain thereof and CO consumption under syngas conditions.
FIG. 2D shows a graph confirming the growth rates of an ECO strain and a parent strain thereof according to CO concentrations.
FIG. 2E shows a graph illustrating the measurement results of the cell densities ($OD_{600}$) of an ECO strain and a parent strain thereof according to CO concentrations.
FIG. 2F shows a graph confirming the acetate production level of an ECO strain and a parent strain thereof according to CO concentrations.

Specifically, in order to determine CO tolerance, *E. limosum* was cultured under the conditions described in Example 1.1 to Example 1.2, and the transfer point of ALE was determined (FIG. 2A). Under this condition, the cell growth rate was 0.070±0.002 $h^{-1}$ and the maximum cell density ($OD_{600}$) was 0.486±0.021. This is different from that the cell growth rate, which was 0.058±0.000 $h^{-1}$ under 40% CO condition, which is because the autotrophic growth of acetogens is enhanced in an environment where $H_2$ is co-present with CO.

According to the growth profile, the mid-exponential phase was 42 to 54 hours after the first inoculation. Therefore, 48 hours was determined as the transfer point of ALE.

In order to perform ALE, four independent *E. limosum* groups (named as ALE1, ALE2, ALE3, and ALE4, respectively) were adapted and their reproducibility was confirmed. First, in the $40^{th}$ generation, the growth rate of all of the groups was increased to 0.085 $h^{-1}$, and this was maintained until the $120^{th}$ generation (FIG. 2B). After adaptation, the growth rate began to show a slight difference at 0.086 $h^{-1}$ in the $120^{th}$ generation, but there was no change after the $150^{th}$ generation (FIG. 2B). Accordingly, ALE was stopped in the $150^{th}$ generation.

To further examine changes in cell growth at the clonal level, the evolved strain ALE4 (hereinafter, ECO), which showed the highest growth rate of 0.089 $h^{-1}$ in the $150^{th}$ generation, was selected. Meanwhile, the other three groups (i.e., ALE1, ALE2, and ALE3) also showed similar growth rates of 0.086 $h^{-1}$, 0.087 $h^{-1}$, and 0.088 $h^{-1}$, respectively.

The growth and CO consumption profiles of ECO and its parent strain were compared under the conditions of syngas (FIG. 2C). The two strains completely consumed the CO present in the head space at 84 and 64 hours, respectively. The CO consumption rates were 0.043±0.019 mmol $h^{-1}$ and 0.058±0.003 mmol $h^{-1}$, respectively. These results indicate that the carbon consumption rate of the adapted strain was increased by 1.35-fold (FIG. 2C).

In addition, it was confirmed that ECO and its parent strain reached the stationary phase at 72 and 48 hours, respectively, and the maximum cell densities ($OD_{600}$) of the strains were increased by 1.28-fold to 0.498±0.028 and 0.639±0.016, respectively (FIG. 2C).

Then, the CO tolerance of ECO was confirmed while changing the CO concentration from 0% to 100%, and the results are shown in FIG. 2D. The growth rates of the strains under the conditions of CO concentrations of 20% and 40% were 0.076±0.001 $h^{-1}$ and 0.089±0.001 $h^{-1}$, respectively, which were 1.21- and 1.56-fold higher compared to that of the parent strain under the same conditions, respectively (FIG. 2D). In addition, the growth rates were 0.069±0.001 $h^{-1}$, 0.056±0.001 $h^{-1}$ and 0.048±0.001 $h^{-1}$, respectively, under the conditions of growth inhibition of 60%, 80%, and 100% CO, which were 1.64-, 1.30-, and 1.20-fold higher compared to that of the parent strain, respectively (FIG. 2D). In addition, the maximum $OD_{600}$ value was confirmed under the condition of CO concentration of 60%, which was 7.49-fold higher compared to that of the parent strain (FIG. 2E).

The amount of acetate produced by ECO at CO concentrations of 0%, 20%, 40%, 80%, and 100% were 0.274±0.060 mM, 3.835±0.215 mM, 6.819±0.457 mM, 8.311±0.254 mM, 0.866±0.217 mM, and 0.264±0.043 mM, respectively (FIG. 2F).

From the above, it was confirmed that the acetate production was dependent on growth in both ECO and its parent strain, but the amount of acetate produced and the growth level were increased in ECO. These results indicate that the amount of CO consumed, the growth, and the tolerance were increased in the adaptively-evolved *E. limosum* under autotrophic conditions.

2.3 Confirmation of Mutations in Adaptive Evolutionary Strains Through Genome Re-Sequencing The genome was analyzed in order to confirm the genetic variation that causes the phenotypic changes shown in Example 2.1. For this purpose, the whole-genome sequencing of the first, the $50^{th}$, the $100^{th}$, and the $150^{th}$ generations was performed, respectively. As a result, it was confirmed that there are a total of 39 mutations in all of the adaptively evolved strains (Table 6).

TABLE 6

| Samples | Locus tag | Position | Type | Reference | Allele | AA change |
|---|---|---|---|---|---|---|
| ECO_acs | ELIM_c1653 | 1,832,907 | SNV | C | T | Ala$^{92}$Val |
| A, 2, 3, 4 | | 1,832,922 | SNV | C | A | Ala$^{97}$Glu |
| 1, 2, 3, 4 | ELIM_c1031 | 1,126,411 | Insertion | — | T | Asn$^{119}$LysfsX132 |
| 1, 2, 3, 4 | Intergenic | 1,970,647 | SNV | G | A | — |
| 1, 2, 3 | ELIM_c1654 | 1,834,784 | Insertion | — | A | Ala$^{72}$AlafsX92 |
| 1, 2, 3 | ELIM_c3581 | 3,896,831 | SNV | C | A | Asp$^{66}$Tyr |
| 1, 2, 3 | Intergenic | 1,972,135 | SNV | T | C | — |
| 1, 2, 4 | ELIM_c1038 | 1,130,590 | SNV | G | A | Glu$^{48}$Lys |
| 1, 2, 4 | ELIM_c1073 | 1,159,055 | SNV | T | G | Tyr$^{136}$X |
| 1, 4 | ELIM_c0527 | 588,552 | Deletion | C | — | Gly$^{279}$ValfsX282 |
| 1 | ELIM_c0236 | 256,802 | SNV | G | T | Ser$^{348}$X |
| 1 | ELIM_c0337 | 370,333 | SNV | C | G | Glu$^{315}$Gln |
| 1 | ELIM_c0437 | 483,053 | SNV | G | A | Ala$^{185}$Val |
| 1 | ELIM_c0530 | 592,464 | SNV | G | A | Ile$^{774}$Ile |
| 1 | ELIM_c0659 | 726,708 | SNV | G | C | Pro$^{74}$Arg |
| | | 726,714 | SNV | T | C | Asp$^{72}$Gly |
| 1 | ELIM_c0672 | 739,966 | SNV | C | A | Ala$^{88}$Ser |
| 1 | ELIM_c0750 | 832,772 | SNV | G | C | Ala$^{326}$Ala |
| 1 | ELIM_c0854 | 938,560 | SNV | A | G | Lys$^{490}$Arg |
| 1 | ELIM_c0866 | 952,049 | SNV | G | A | Val$^{789}$Val |
| 1 | ELIM_c1063 | 1,148,482 | SNV | G | T | Gly$^{741}$Trp |
| 1 | ELIM_c1325 | 1,436,020 | SNV | A | G | Ile$^{865}$Thr |
| 1 | ELIM_c2814 | 3,101,419 | SNV | C | A | Ala$^{63}$Ala |
| 1 | ELIM_c2882 | 3,162,881 | SNV | G | A | Gly$^{38}$Arg |
| 1 | ELIM_c2942 | 3,240,199 | SNV | C | A | Arg$^{143}$Arg |
| 1 | ELIM_c3150 | 3,443,977 | SNV | T | C | Asp$^{310}$Gly |
| 1 | ELIM_c3386 | 3,699,117 | SNV | T | A | Leu$^{144}$X |
| 1 | ELIM_c3427 | 3,747,388 | SNV | G | T | Asp$^{56}$Tyr |
| 1 | ELIM_c3691 | 3,999,914 | SNV | C | A | Met$^{194}$Ile |
| 1 | Intergenic | 3,309,964 | SNV | A | T | — |
| 2 | ELIM_c2071 | 2,255,729 | SNV | C | A | Gly$^{14}$Val |
| 2 | ELIM_c2621 | 2,852,312 | SNV | G | C | Leu$^{152}$Leu |
| 2 | ELIM_c3002 | 3,306,141 | SNV | C | T | Ser$^{47}$Ser |
| 2 | Intergenic | 3,183,238 | SNV | G | C | — |
| 2 | Intergenic | 3,305,753 | SNV | G | A | — |
| 3 | ELIM_c0293 | 322,696 | SNV | G | T | Ile$^{170}$Ile |
| 4 | ELIM_c0006 | 5,401 | SNV | G | T | His$^{99}$Asn |
| 4 | ELIM_c1330 | 1,446,536 | SNV | G | A | Val$^{392}$Val |
| 4 | Intergenic | 1,946,081 | SNV | G | C | — |

As a result of classification of these mutations, it was confirmed that 33 mutations were located in the genic regions and that 6 mutations were located in the intergenic regions.

Among these, five key mutations accounting for the mutation frequency of top 15% were confirmed. These were confirmed as single base mutations (SNV) (i.e., ELIM_c1038, ELIM_c1073, and ELIM_c1653) and insertion mutations (i.e., ELIM_c1031 and ELIM_c1654) (Table 7).

TABLE 7

| Locus Tag | Gene | Mutation (Type) | AA Change | Description |
|---|---|---|---|---|
| ELIM_c1031 | — | —356T (insertion) | Asn$^{119}$LysfsX133 | Integrase family protein |
| ELIM_c1038 | — | G133A (SNV) | Glu48Lys | Putative ATPase, transposase-like protein |
| ELIM_c1073 | dam | T408G (SNV) | Tyr$^{136}$X | N6 adenine-specific DNA methylase D12 class |
| ELIM_c1653 | acsA | C290A (SNV) | Ala97Glu | CODH catalytic subunit |
| ELIM_c1654 | cooC2 | —216A (insertion) | Ala$^{72}$AlafsX92 | CODH nickel insertion accessory protein |

It was confirmed that two kinds of the above mutations were located in hypothetical genes, while the other three kinds were located in the genes whose functions are identified. In particular, it was confirmed that the two kinds of mutations are mutations in an active site and in a major region that determines maturity in acsA and cooC2 genes, which are the genes encoding the CODH/ACS complex.

Specifically, it was assumed that although the mutation of acsA is not located in the active site of the enzyme, it may modify the structure of the protein by mutating a small non-polar amino acid into a large polar amino acid thereby affecting the activity of the protein. The other mutation occurred in cooC2 appeared as a synonymous substitution at the mutation site, but it induced a frame shift and thereby introduced an early stop codon 20 amino acids downstream of the mutation site. Considering that an early stop codon usually leads to a loss of gene function, this may be interpreted as having no effect in evolved strains regardless of the importance of cooC in autotrophic conditions.

Based on the foregoing, it was interpreted that the mutation in the acsA gene, among the 5 major mutations, represents the altered phenotype of the strain that is adapted/evolved to autotrophic growth.

2.4 Effect of acsA Mutation on CO Fixation

In order to verify the details confirmed in Example 2.3, additional experiments were performed.

Figures 3A, 3B, 3C, 3D:
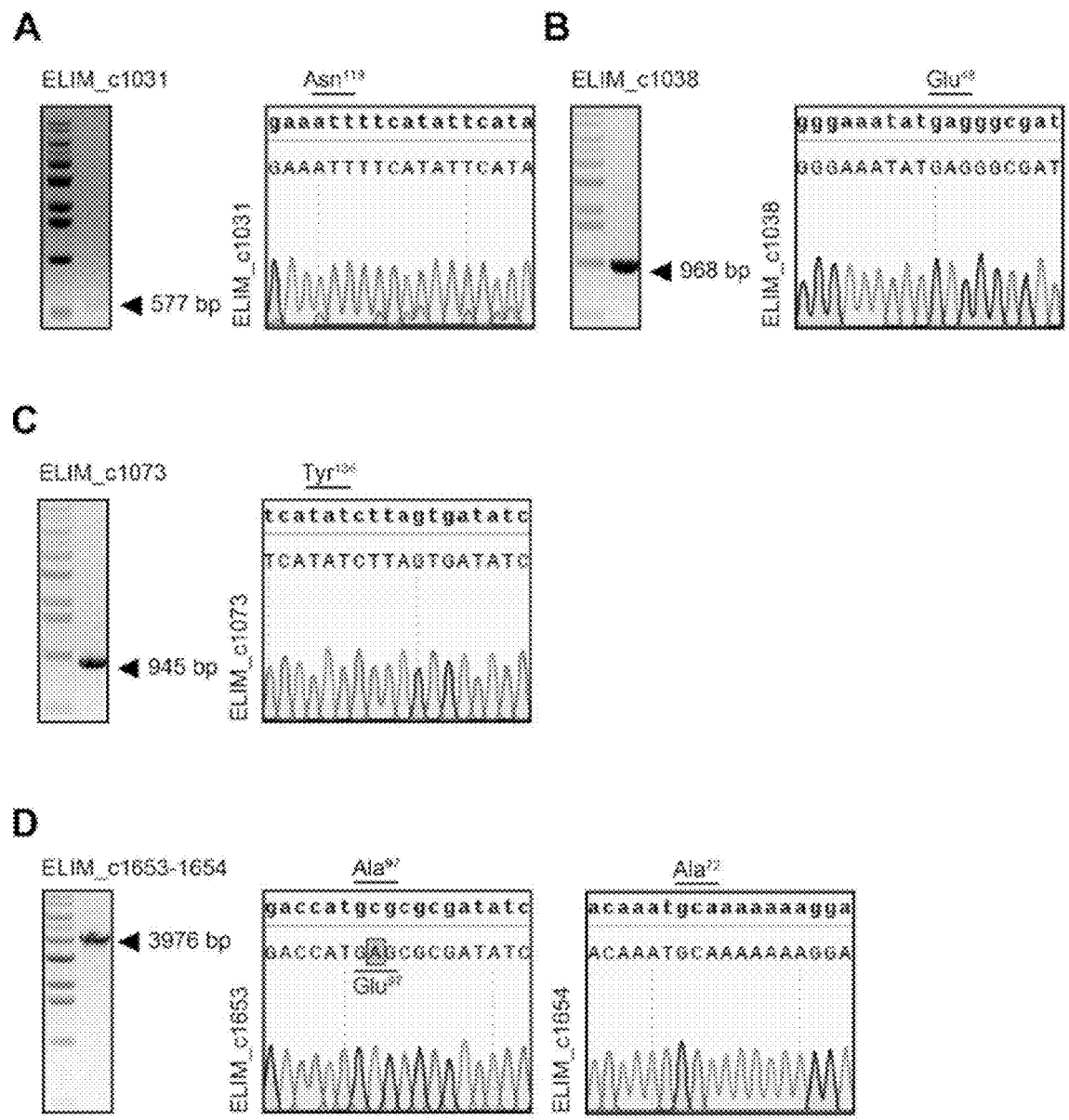
FIGS. 3A-3D shows images confirming that a mutation, among the five kinds of key mutations, is included only in the acsA gene within the ECO_acsA, compared to the reference.
Figure 4:
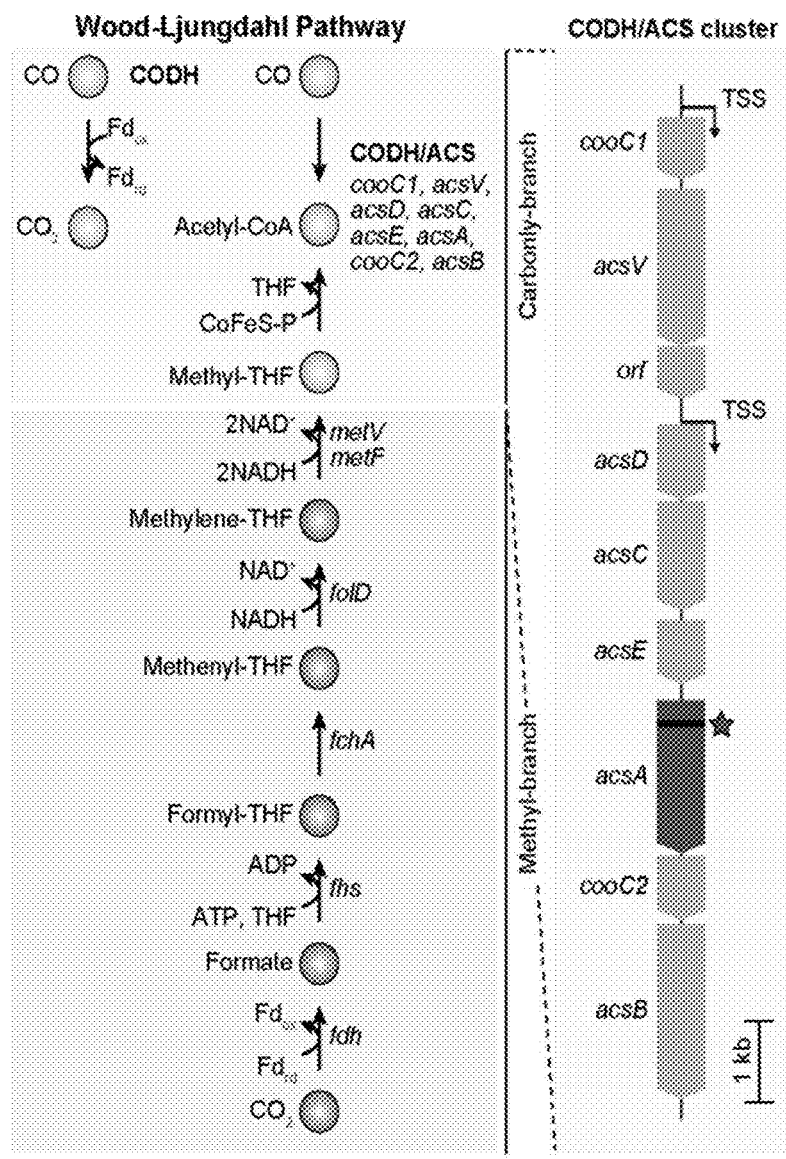
FIG. 4 shows the Wood-Ljungdahl pathway of E. limosum and a schematic diagram illustrating a gene cluster involved in the Wood-Ljungdahl pathway, in which the region where a mutation has occurred is indicated with a star.

Among the 5 mutations identified in Example 2.3 above, the mutant strain, which has a mutation only in the acsA gene but has no mutations in the other four kinds of genes, was isolated (FIG. 3) and was named as ECO_acsA. This mutant strain was deposited at the Korean Culture Center of Microorganisms (KCCM) of the Korea Research Institute of Bioscience and Biotechnology (KRIBB) on Jun. 4, 2020, and was assigned Accession No. KCTC 14201BP.

Meanwhile, it was confirmed that the ECO_acsA further includes other mutations in addition to the mutation of the acsA gene, but it was confirmed that the other mutations were mutations that could not have an effect on autotrophic growth conditions. These mutations included in the ECO_acsA are described in Table 8 below.

TABLE 8

| Locus Tag | Gene | Mutation (Type) | AA Change | Description |
|---|---|---|---|---|
| ELIM_c0006 | — | G1265T (SNV) | Ala$^{422}$Glu | Gp11 |
| ELIM_c2214 | — | —413G (insertion) | Arg$^{138}$Arg | Hypothetical protein |
| ELIM_c2227 | — | G82T (SNV) | Ala$^{28}$Ser | Terminase |
| ELIM_cl653 | acsA | C290A (SNV) | Ala$^{97}$Glu | CODH Catalytic subunit |
| Intergenic | — | C2393145— (deletion) | — | — |
|  | — | A2393154— (deletion) | — | — |

Figures 5A, 5B, 5C:
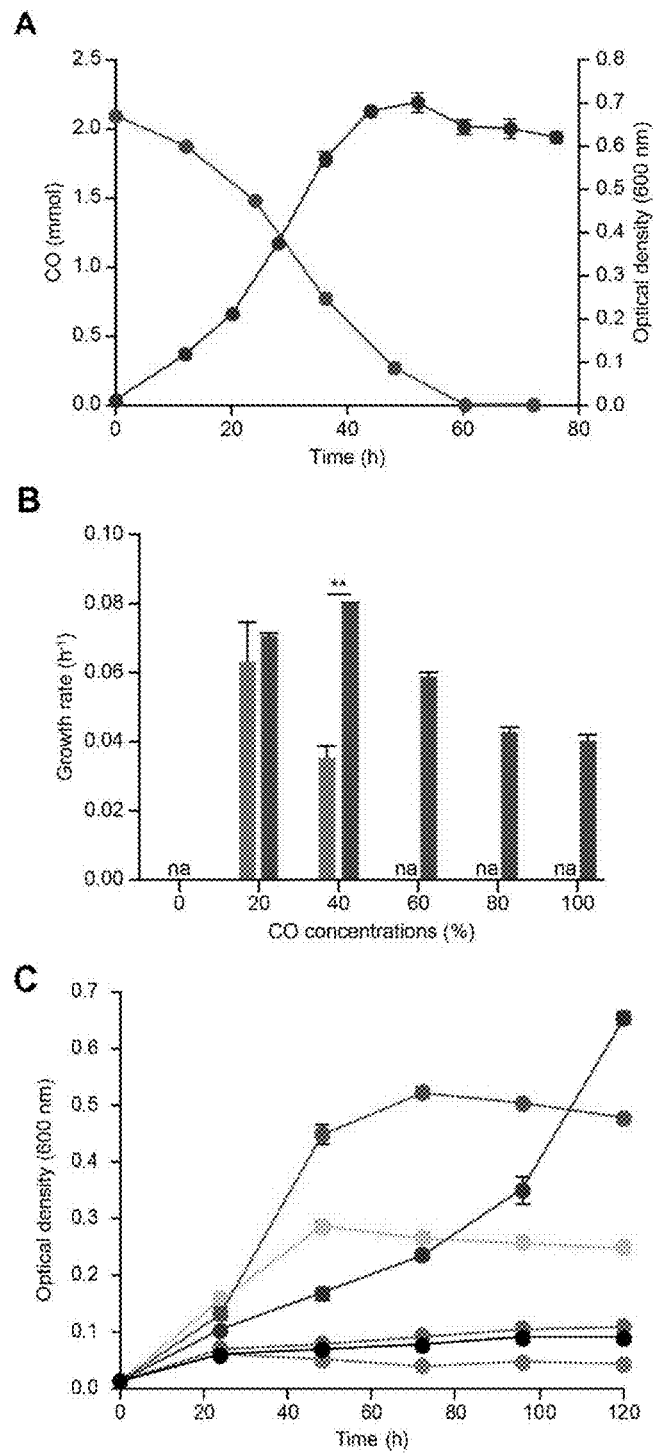
FIG. 5A shows a graph illustrating the measurement results of the cell growth rates and cell densities of the ECO_acsA strain and a parent strain thereof under syngas conditions comprising 44% of CO.
FIG. 5B shows a graph illustrating the measurement results of the cell growth rates of the ECO_acsA strain and a parent strain thereof under the conditions of CO concentrations of 0%, 20%, 40%, 60%, 80%, and 100%, respectively.
FIG. 5C shows a graph illustrating the measurement results of the cell densities ($OD_{600}$) of the ECO_acsA strain and a parent strain thereof under the conditions of CO concentrations of 0%, 20%, 40%, 60%, 80%, and 100%, respectively.

An experiment to confirm the CO availability of the isolated ECO_acsA strain was performed. First, the growth profile of the isolated ECO_acsA strain was confirmed under the syngas conditions in the presence of 44% CO and then compared to that of the parent strain. In the ECO_acsA strain and its parent strain, the growth rates were 0.095±0.000 h$^{-1}$ and 0.050±0.001 h$^{-1}$, respectively, and the cell densities were 0.703±0.023 and 0.498±0.028, respectively (FIG. 5A). These results indicate that the ECO_acsA strain grows 1.9-fold faster and thus has a 1.41-fold higher cell density compared to its parent strain.

Then, the production of metabolites and CO consumption by the ECO_acsA strain were measured under syngas conditions in the presence of 44% CO. As confirmed previously in the Examples, acetate was the main product, and the amount of acetate produced was 6.889 mM. Such an increase in the amount of acetate produced indicates that the C-cluster in the active site of the CODH subunit, which is encoded by the mutated acsA, increases CO utilization. As in the amount of acetate produced, CO consumption rates in the ECO_acsA strain and its parent strain were 0.059±0.002 mmol h$^{-1}$ and 0.043±0.019 mmol 11$^{-1}$, respectively, thus showing a difference of about 1.37-fold (FIG. 5A).

Then, CO tolerance was measured at different CO concentrations. Under the conditions of CO concentrations of 20%, 40%, 60%, 80%, and 100%, the growth rate of the ECO_acsA strain was 0.070±0.001 h$^{-1}$, 0.079±0.001 h$^{-1}$, 0.059±0.001 h$^{-1}$, 0.043±0.002 h$^{-1}$, and 0.040±0.001 h$^{-1}$, respectively, indicating that the growth rate gradually decreased at a CO concentration of 40% or higher (FIG. 5B). However, it was confirmed that the decreased growth rate was also an increase compared to that of the parent strain, and the growth rate was increased by 2.25-fold under the conditions of 40% CO. In addition, it was confirmed that in all of the CO conditions, the cell density of the ECO_acsA strain was increased compared to that of its parent strain (FIG. 5C). These results indicate that the CO resistance of the strain was increased significantly.

These results, as predicted in Example 2.3, confirm that the phenotypic changes in *E. limosum* that appear when the microorganism is cultured under CO conditions are due to the mutation of acsA, and it can be seen that the acsA mutation is a key factor in the strain's utilization of CO.

2.5 Amount of Acetoin Produced by ECO_acsA Strain

The genes involved in the acetoin biosynthesis pathway are present in *E. limosum*, but the production of acetoin under CO or glucose, and H$_2$/CO$_2$ conditions has not been confirmed. This was thought to be because insignificant transcription and translation are blocked when *E. limosum* is cultured under heterotrophic or eutrophic conditions. Therefore, whether it is possible to synthesize acetoin from the new biosynthetic pathway, that was confirmed based on the previous Examples, was confirmed.

In order to synthesize acetoin, a plasmid, which includes alsS encoding α-acetolactate synthase (which produces one molecule of acetolactate by condensation of two molecules of pyruvic acid) and alsD encoding acetolactate decarboxylase (which converts acetolactate to acetoin), was constructed (FIG. 6A), and the plasmid was introduced into the parent strain by transformation. The specific method for plasmid construction is described in Example 1.6, and the method for strain preparation is described in Example 1.7.

Figures 6A, 6B:
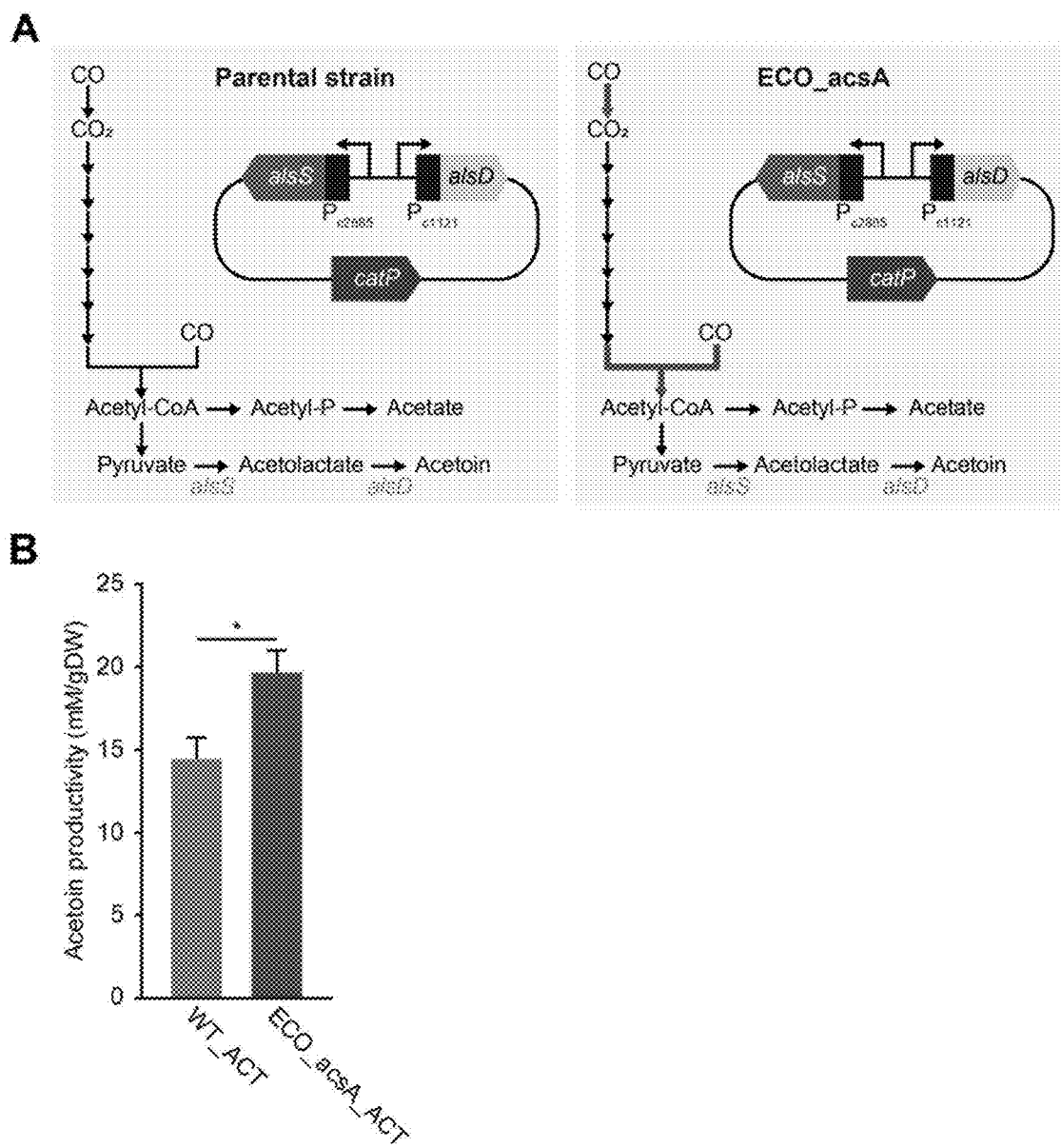
FIGS. 6A-6B shows pathways illustrating the synthesis of acetoin from CO in the ECO_acsA strain (ECO_acsA_ACT), into which a plasmid encoding alsS and alsD genes are introduced, and from CO in a parent strain thereof (WT_ACT), into which the plasmid is introduced (FIG. 6A), and the amounts of acetoin produced from each strain above (FIG. 6B).

The prepared strain (WT_ACT) was cultured in syngas conditions in the presence of 44% CO (performed in three repetitions), and it was confirmed that acetoin was produced in an amount of 14.6±0.8 mM/gDW (FIG. 6B).

The same plasmid was introduced into the ECO_acsA strain (ECO_acsA_ACT) and the amount of metabolites produced was measured under the same CO condition. As a result, it was confirmed that the amount of acetoin produced was 19.6±1.3 mM/gDW, which is an increase by 1.34-fold (P-value≤0.015).

In addition, as a result of comparison of the amount of CO consumed, it was confirmed that the WT_ACT consumed CO in the amount of 429.8±131.6 mM/gDW, and the ECO_acsA_ACT consumed CO in the amount of 642.7±317.8 mM/gDW. That is, it can be interpreted that the ECO_acsA strain has increased CO resistance and CO consumption, and thus has an enhanced ability of producing acetoin.

To summarize the above, it was confirmed that the mutations in the CODH/ACS complex can increase CO tolerance, CO consumption, and growth rates of strains in the presence of CO, and can be effectively used in the design of strains. Therefore, it can be seen that these mutations can also be applied to the production of useful products such as acetoin.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims

[Accession No.]
Depositary: Korea Research Institute of Bioscience and Biotechnology
Accession Number: KCTC14201BP
Deposited Date: Jun. 4, 2020

---

The invention claimed is:

1. A protein variant having carbon monoxide dehydrogenase activity, wherein the 97$^{th}$ residue from the N-terminus of SEQ ID NO: 1, alanine (A), is substituted with a different amino acid, and wherein the different amino acid is selected from the group consisting of aspartic acid (D), glutamic acid (E), lysine (K), arginine (R), histidine (H), tyrosine (Y), asparagine (N), glutamine (Q), tryptophan (W), phenylalanine (P), methionine (M), and proline (P).

2. The protein variant of claim 1, wherein the different amino acid is glutamic acid (E).

3. The protein variant of claim 1, wherein the protein variant is encoded by a nucleotide sequence having a substitution at position 290 of SEQ ID NO: 2.

* * * * *